US011650195B2

(12) United States Patent
Kaditz et al.

(10) Patent No.: US 11,650,195 B2
(45) Date of Patent: May 16, 2023

(54) ITERATIVE MEDICAL TESTING OF BIOLOGICAL SAMPLES

(71) Applicant: Q Bio, Inc, San Carlos, CA (US)

(72) Inventors: Jeffrey Howard Kaditz, Wilson, WY (US); Andrew Gettings Stevens, New York, NY (US)

(73) Assignee: Q Bio, Inc., San Carlos, CA (US)

( * ) Notice: Subject to any disclaimer, the term of this patent is extended or adjusted under 35 U.S.C. 154(b) by 1218 days.

(21) Appl. No.: 16/142,554

(22) Filed: Sep. 26, 2018

(65) Prior Publication Data

US 2019/0025280 A1   Jan. 24, 2019

Related U.S. Application Data

(63) Continuation-in-part of application No. 15/461,429, filed on Mar. 16, 2017, now abandoned.

(60) Provisional application No. 62/454,707, filed on Feb. 3, 2017.

(51) Int. Cl.
  *G01N 33/487* (2006.01)
  *G16H 30/20* (2018.01)
  *H04L 9/32* (2006.01)
  *G16H 50/50* (2018.01)
  *H04L 9/06* (2006.01)
  *G16H 20/00* (2018.01)
  *G16H 30/40* (2018.01)
  *H04L 9/00* (2022.01)

(52) U.S. Cl.
  CPC ....... *G01N 33/48792* (2013.01); *G16H 30/20* (2018.01); *G16H 50/50* (2018.01); *H04L 9/3239* (2013.01); *G16H 20/00* (2018.01); *G16H 30/40* (2018.01); *H04L 9/0643* (2013.01); *H04L 9/50* (2022.05)

(58) Field of Classification Search
  None
  See application file for complete search history.

(56) References Cited

U.S. PATENT DOCUMENTS

| | | | |
|---|---|---|---|
| 4,729,892 A | 3/1988 | Beall | |
| 5,793,210 A | 8/1998 | Pla | |
| 6,084,408 A | 7/2000 | Chen | |
| 6,148,272 A | 11/2000 | Bergstrom | |
| 6,392,409 B1 | 5/2002 | Chen | |
| 7,924,002 B2 | 4/2011 | Lu | |
| 7,940,927 B2 | 5/2011 | Futa | |
| 7,974,942 B2 | 7/2011 | Pomroy | |
| 8,432,165 B2 | 4/2013 | Weiger Senften | |
| 8,502,532 B2 | 8/2013 | Assmann | |
| 8,686,727 B2 | 4/2014 | Reddy | |
| 8,723,518 B2 | 5/2014 | Seiberlich | |
| 8,736,265 B2 | 5/2014 | Boernert | |
| 9,513,359 B2 | 12/2016 | Koch | |
| 9,514,169 B2 | 12/2016 | Mattsson | |
| 2002/0155587 A1 | 10/2002 | Opalsky | |
| 2002/0177771 A1 | 11/2002 | Guttman | |
| 2003/0210043 A1 | 11/2003 | Freedman | |
| 2005/0137476 A1 | 6/2005 | Weiland | |
| 2005/0181466 A1 | 8/2005 | Dambinova | |
| 2008/0065665 A1 | 3/2008 | Pomroy | |
| 2008/0081375 A1 | 4/2008 | Tesiram | |
| 2008/0082834 A1 | 4/2008 | Mattsson | |
| 2009/0315561 A1 | 12/2009 | Assmann | |
| 2010/0131518 A1 | 5/2010 | Elteto | |
| 2010/0142823 A1 | 6/2010 | Wang | |
| 2010/0177188 A1 | 7/2010 | Kishima | |
| 2010/0189328 A1 | 7/2010 | Boernert | |
| 2010/0244827 A1 | 9/2010 | Hennel | |
| 2010/0306854 A1 | 12/2010 | Neergaard | |
| 2011/0095759 A1 | 4/2011 | Bhattacharya | |
| 2011/0166484 A1 | 7/2011 | Virta | |
| 2012/0124161 A1 | 5/2012 | Tidwell | |
| 2013/0275718 A1 | 10/2013 | Ueda | |
| 2013/0294669 A1 | 11/2013 | El-Baz | |
| 2013/0338930 A1 | 12/2013 | Senegas | |
| 2014/0062475 A1 | 3/2014 | Koch | |
| 2014/0336998 A1 | 11/2014 | Cecchi | |

(Continued)

FOREIGN PATENT DOCUMENTS

| | | |
|---|---|---|
| EP | 1953580 | 9/2014 |
| EP | 3093677 | 11/2016 |

(Continued)

OTHER PUBLICATIONS

U.S. Appl. No. 15/169,719, filed May 31, 2016, Fast Scanning Based on Magnetic-Resonance History.
U.S. Appl. No. 15/499,004, filed Apr. 27, 2017, Uniform-Frequency Records With Obscued Context.
U.S. Appl. No. 15/299,337, filed Oct. 20, 2016, Population-Based Medical Rules Via Anonymous Sharing.
U.S. Appl. No. 16/085,877, filed Sep. 17, 2018, System and Method for Magnetic Resonance Elastography.
U.S. Appl. No. 15/362,808, filed Nov. 28, 2016, Tensor Field Mapping.
U.S. Appl. No. 15/362,813, filed Nov. 28, 2016, Rapid Determination of A Relaxation Time.
U.S. Appl. No. 15/461,429, filed Mar. 16, 2017, Iterative Medical Testing of Biological Samples.
U.S. Appl. No. 15/924,050, filed Mar. 16, 2018, User Interface for Medical Information.

(Continued)

*Primary Examiner* — Lori A. Clow
(74) *Attorney, Agent, or Firm* — Aurora Consulting LLC

(57) ABSTRACT

A system performs one or more magnetic resonance (MR) measurements on at least a portion of a biological life form. Moreover, the system quantitatively simulates an MR response of at least the portion of the biological life form, and compares the one or more MR measurements and the quantitative simulation to obtain a first test result. Next, the system determines one or more additional medical tests to perform. In response, the system accesses the biological sample in storage, and performs the one or more additional medical tests on at least a second portion of the biological sample to obtain one or more additional test results. Furthermore, the system computes a second test result based at least in part on the first test result and the one or more additional test results, where the second test result has an improved accuracy relative to the first test result.

20 Claims, 10 Drawing Sheets

(56) References Cited

U.S. PATENT DOCUMENTS

| | | | |
|---|---|---|---|
| 2015/0003706 | A1 | 1/2015 | Eftestøl |
| 2015/0032421 | A1 | 1/2015 | Dean |
| 2015/0040225 | A1 | 2/2015 | Coates |
| 2015/0089574 | A1 | 3/2015 | Mattsson |
| 2016/0007968 | A1 | 1/2016 | Sinkus |
| 2016/0127123 | A1 | 5/2016 | Johnson |
| 2017/0011514 | A1 | 1/2017 | Westerhoff |
| 2017/0038452 | A1 | 2/2017 | Trzasko |

FOREIGN PATENT DOCUMENTS

| | | |
|---|---|---|
| WO | WO-2014205275 | 12/2014 |
| WO | WO-2015183792 | 12/2015 |
| WO | WO-2016073985 | 5/2016 |

OTHER PUBLICATIONS

"International Application Serial No. PCT/US2017/022842, International Search Report dated May 23, 2017, PCT search report May 23, 2017", 2 pgs.

"International Application Serial No. PCT/US16/040215, Written Opinion dated Sep. 19, 2016, Other Description Mar. 1, 2017", 9 pgs.

"International Application Serial No. PCT/US16/51204, International Search Report dated Nov. 28, 2016, Other Description Mar. 1, 2017", 2 pgs.

"International Application Serial No. PCT/US2017/022842, Written Opinion dated May 23, 2017, PCT report opinion May 23, 2017", 4 pgs.

"International Application Serial No. PCT/US16/51204, Written Opinion dated Nov. 28, 2016, Other Description Mar. 1, 2017", 10 pgs.

Drescher et al., article titled "Longitudinal Screening Algorithm That Incorporates Change Over Time in CA125 Levels Identifies Ovarian Cancer Earlier Than a Single-Threshold Rule," Journal of Clinical Oncology, vol. 31, No. 3, Jan. 20, 2013, pp. 387-392.

"I. Kononenko "Machine learning for medical diagnosis: history, state of the art and perspective" Artificial Intelligence in Medicine 23 (2001) 21 pgs , Non-final office action dated Mar. 8, 2018".

"International Application Serial No. PCT/US2016/040215, International Preliminary Report on Patentability and Written Opinion dated Jan. 9, 2018, Other Description Jan. 9, 2018".

"Kwan et al: "MRI Simulation-Based Evaluation of Image-Processing and Classification Methods" IEEE Transactions on Medical Imaging, vol. 18 No. 11, Nov. 1999, , Final office action dated Jun. 28, 2018", 13 pgs.

International Application Serial No. PCT/US2017/035073, International Search Report dated Aug. 11, 2017, 2 pgs.

International Application Serial No. PCT/US2017/035071, International Search Report dated Aug. 22, 2017, 2 pgs.

International Application Serial No. PCT/US2017/035073, Written Opinion dated Aug. 11, 2017, 6 pgs.

International Application Serial No. PCT/US2017/035071, Written Opinion dated Aug. 22, 2017, 7 pgs.

Gualda et al., "SPIM-fluid: open source light-sheet based platform for high-throughput imaging", Biomed Opt Express (Nov. 1, 2015) vol. 6, No. 11, 10 pages.

International Application Serial No. PCT/US2017/022911, International Search Report dated Jul. 19, 2017, 4 pgs.

International Application Serial No. PCT/US2017/022911, Written Opinion dated Jul. 19, 2017, 10 pgs.

ITERATIVE MEDICAL TESTING OF BIOLOGICAL SAMPLES

CROSS-REFERENCE TO RELATED APPLICATION

This application claims priority under 35 U.S.C. 120 as a Continuation-in-Part of U.S. patent application Ser. No. 15/461,429, "Iterative Medical Testing of Biological Samples," filed on Mar. 16, 2017, and claims priority under 35 U.S.C. 119(e) to U.S. Provisional Application Ser. No. 62/454,707, entitled "System and Method for Ordering Medical Tests," by Jeffrey H. Kaditz and Andrew G. Stevens, filed on Feb. 3, 2017, the contents of both of which are hereby incorporated by reference.

FIELD

The described embodiments relate to medical testing of biological samples, which were acquired at different times, in order to reduce an uncertainty of test results.

RELATED ART

Medical or medical tests of biological samples are widely used by healthcare providers (such as physicians). For example, a physician may order biochemical, metabolic, molecular and/or cellular analysis of a biological sample from or associated with a patient. The results of the medical tests are typically used to diagnosis patients and to guide or inform subsequent treatment decisions.

Often, determination of a diagnosis and treatment are interrelated. For example, an iterative problem-solving process may be used. During this iterative problem-solving process, the results of initial medical tests are used to formulate a potential diagnosis and treatment plan. In turn, the response of the patient to the treatment may be used to refine the potential diagnosis and to guide the selection of additional medical testing. Ideally, the iterative problem-solving process converges on a solution in a timely and cost-effective manner.

However, in practice, the iterative problem-solving process can be time consuming and expensive. This is because of the need to subsequently acquire additional biological samples over time as the patient's condition evolves, and because of diagnostic and treatment uncertainties. Moreover, while a physician converges on a diagnostic and treatment solution, patient suffering and mortality can occur.

SUMMARY

A first group of described embodiments relates to a system (or an electronic device) that performs a medical test. For example, the system may include: an interface circuit that communicates with at least another electronic device; a processor; and memory that stores program instructions that can be executed by the processor. During operation, the system stores a biological sample associated with a biological life form. Then, the system performs one or more magnetic resonance (MR) measurements on at least a portion of the biological life form using an MR measurement device. Moreover, the system quantitatively simulates an MR response of at least the portion of the biological life form, and compares the one or more MR measurements and the quantitative simulation to obtain a first test result. Next, the system determines one or more additional medical tests to perform that can improve an accuracy of the first test result. Furthermore, the system accesses the biological sample to obtain at least a second portion of the biological sample, and performs the one or more additional medical tests on at least the second portion of the biological sample to obtain one or more additional test results. Additionally, the system computes a second test result based at least in part on the first test result and the one or more additional test results, where the second test result has an improved accuracy relative to the first test result.

Note that the biological sample may be stored in a repository, such as a cryogenic repository. Moreover, the storing may involve dividing and separately storing two or more portions of the sample. In some embodiments, storing the biological sample may involve storing a longitudinal sequence of biological samples associated with the biological life form over a time interval.

Furthermore, the determining may involve assessing benefits of a set of additional medical tests relative to costs of the set of additional medical tests and selecting the one or more additional medical tests. For example, the cost may include an opportunity cost of potential future use of the biological sample, because only a finite amount of material may be included in the biological sample that is in store.

Note that the one or more additional medical tests may be performed automatically by the system.

Additionally, the one or more additional medical tests may include: a genetic test, a metabolic test, a biochemical test, a molecular test and/or cellular analysis.

In some embodiments, the quantitative simulation may involve a forward calculation based at least in part on an invariant MR signature of at least the portion of the biological sample, a pulse sequence, a magnetic-field strength, a magnetic-field gradient, magnetic-field inhomogeneities of the MR measurement device, and/or a noise characteristic of the MR measurement device. Note that the invariant MR signature may characterize an MR response of at least the portion of the biological sample to MR measurement conditions that comprise a given pulse sequence, a given magnetic-field strength and/or a given magnetic-field gradient selected from a range of pulse sequences, a range of magnetic-field strengths and/or a range of magnetic-field gradients.

Moreover, the invariant MR signature may be determined using an inverse calculation based at least in part on additional MR measurements on at least the portion of the biological sample or a different portion of the biological sample and the MR measurement conditions.

Furthermore, the system may provide a recommendation based at least in part on the second test result when the improved accuracy is less than a threshold value.

Additionally, the accessing may involve accessing one of a set of portions of the sample having a predefined aliquoted amount needed for the one or more additional medical tests.

A second group of described embodiments relates to a system that iteratively performs medical testing. During operation, the system receives a test result of a medical test performed on a biological sample associated with an individual, where the test result has an initial uncertainty. Then, the system determines, based on the test result, a second medical test to perform on a second biological sample associated with the individual, where the second biological sample was acquired prior to the biological sample. Moreover, the system performs the second medical test on the second biological sample to obtain a second test result of the second medical test. Next, the system computes a revised result for the medical test based on the test result and the second test result, where the revised result has a second uncertainty that is less than the initial uncertainty.

For example, the initial uncertainty or the second uncertainty may correspond to a sensitivity and/or a specificity.

Furthermore, the system may: receive an instruction to perform the medical test on the biological sample; and provide the instruction to perform the medical test on the biological sample.

Additionally, performing the second medical test may involve accessing the second biological sample in a storage repository. Alternatively, performing the second medical test may involve: providing an instruction to perform the second medical test; and receiving the second test result.

In some embodiments, the system provides the revised result.

Note that the determination may be based on a group of biological samples that were previously acquired from the individual and that are available for additional medical testing, where the group of biological samples includes the second biological sample. Moreover, the determination may be based on how the group of biological samples were prepared prior to storage.

Moreover, one or more additional instances of the determining, the performing and the computing may be performed in a temporal sequence over a time interval.

Furthermore, the system may determine a diagnosis for a condition of the individual based on the revised results when the second uncertainty is less than a threshold.

Additionally, the second biological sample may include a temporal sequence of biological samples acquired over a time interval and the second medical test may be performed on the sequence of biological samples.

A third group of embodiments relates to a system that orders medical tests on biological samples.

Another embodiment provides a computer-readable storage medium for use with the system (or the electronic device). This computer-readable storage medium may store a program module, which, when executed by the system, causes the system to perform at least some of the aforementioned operations in the first group of embodiments, the second group of embodiments and/or the third group of embodiments.

Another embodiment provides a method, which may be performed by the system (or the electronic device). This method includes at least some of the aforementioned operations in the first group of embodiments, the second group of embodiments and/or the third group of embodiments.

The preceding summary is provided as an overview of some exemplary embodiments and to provide a basic understanding of aspects of the subject matter described herein. Accordingly, the above-described features are merely examples and should not be construed as narrowing the scope or spirit of the subject matter described herein in any way. Other features, aspects, and advantages of the subject matter described herein will become apparent from the following Detailed Description, Figures, and Claims.

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

Figure 1:
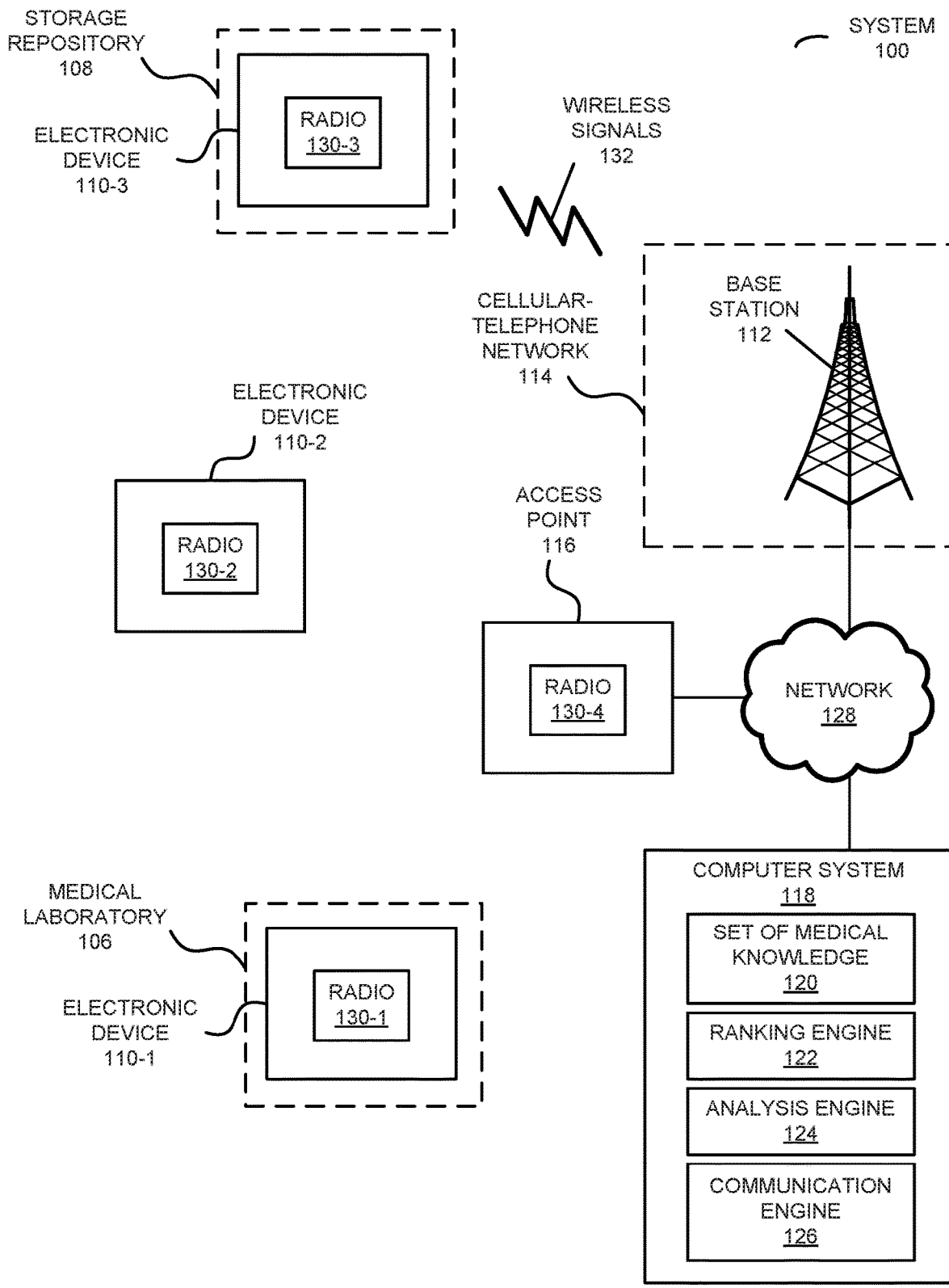
FIG. 1 is a block diagram illustrating an example of a system that performs medical testing in accordance with some embodiments.

In a first group of embodiments, a system that performs one or more MR measurements on at least a portion of a biological life form is described. This system quantitatively simulates an MR response of at least the portion of the biological life form, and compares the one or more MR measurements and the quantitative simulation to obtain a first test result. Next, the system determines one or more additional medical tests to perform. In response, the system accesses the biological sample in storage (e.g., in cryogenic storage), and performs the one or more additional medical tests on at least a second portion of the biological sample to obtain one or more additional test results. Furthermore, the system computes a second test result based at least in part on the first test result and the one or more additional test results, where the second test result has an improved accuracy relative to the first test result.

By iteratively performing the medical testing of a previously acquired and stored biological sample, this testing technique may allow a diagnosis and/or a treatment for the individual to be rapidly and accurately determined. This capability may reduce the overall cost of the medical testing and the treatment. Moreover, in the process, the testing technique may reduce patient suffering and mortality. In addition, the testing technique may allow the stored biological sample to be selectively accessed and used when needed (such as when the one or more additional medical tests are needed, e.g., when the first test result has serious implications or treatment consequences and the remaining uncertainty or the current accuracy of the first test result justifies accessing the limited resource of the stored biological sample). In these ways, the testing technique may improve patient health and outcomes, while protecting or preserving the stored biological sample for future use.

In a second group of embodiments, a system that iteratively performs medical testing is described. During operation, the system receives a test result of a medical test performed on a biological sample associated with an individual, where the test result has an initial uncertainty. Then, the system determines, based on the test result, a second medical test to perform on a second biological sample associated with the individual, where the second biological sample was acquired prior to the biological sample. Moreover, the system performs the second medical test on the second biological sample to obtain a second test result of the second medical test. Next, the system computes a revised result for the medical test based on the test result and the second test result, where the revised result has a second uncertainty that is less than the initial uncertainty.

By iteratively performing the medical testing of a previously acquired and stored biological sample, this testing technique may allow a diagnosis and/or a treatment for the individual to be rapidly and accurately determined. This capability may reduce the overall cost of the medical testing and the treatment. Moreover, in the process, the testing technique may reduce patient suffering and mortality.

In a third group of embodiments, a system that performs ranking of medical tests and then orders one or more medical tests on one or more biological samples according to their rank is described. Notably, the system may rank the medical tests based on their marginal information value, which may be calculated using current information (such as current test results) and historical information (such as previously available information). Moreover, the system may use historical biological samples or historical medical information to further refine a diagnosis. Note that the ranking may have multiple goals, multiple rankings may be created and multiple tests may be ordered based on one or more rankings. For example, if a patient's test result indicates a probability of three conditions, A, B or C, and condition C is potentially fatal, the system may provide higher rankings to medical tests that differentiate condition C from condition A or B and that are known to practitioners, in data structures or databases, or in the medical literature to increase the confidence that a patient does not have condition C. The highest-ranking medical tests may be ordered by a healthcare practitioner, or a medical test may be ordered directly by the system, such as via email or using an Application Programming Interface (API) call to a medical testing provider (such as a testing laboratory) via a network. The tests results may be received via email, via an API and/or may be entered into the system by a healthcare practitioner. Then, the system may update a diagnosis or a risk assessment may be updated using the new information. The improvements in diagnosis and treatment may reduce morbidity and mortality, and may reduce the cost of illness and its treatment.

Note that the use of historical biological samples can enable medical testing of biological samples that were previously acquired and stored before certain medical tests were discovered. In addition, the use of previous biological samples may allow test results to be placed in historical context, such as when a condition appeared in a patient or subject, and the information in a historical pathological model can be used by both doctors and patients alike to improve quality of life and outcomes.

By ordering or requesting the medical tests, this testing technique may enable a patient or a healthcare practitioner to collect more information (e.g., broadly by asking questions about their health or the health of a patient), and/or to refine a diagnosis, such as by performing monitoring using current information and past information (including past or previously acquired biological samples). For example, processing historical blood samples with a new type of blood test may be used to detect the historical onset of a disease.

The use of such a 'time machine' diagnostic capability may, in an efficient and cost-effective manner, increase healthcare-practitioner confidence (e.g., repeatable scientific evidence over time) and may reduce patient fear or anxiety.

In the discussion that follows, an individual or a user may be a person. Moreover, the testing technique may be used by any type of organization, such as a business, which should be understood to include for-profit corporations, non-profit corporations, groups (or cohorts) of individuals, sole proprietorships, government agencies, partnerships, etc. While the testing technique may be used in a wide variety of applications, in the discussion that follows the testing technique is used in healthcare to perform medical testing (which is sometimes referred to as 'clinical testing' or 'laboratory testing'). A medical test may be performed: in a clinical setting (such as a hospital or a clinical laboratory), in an out-patient setting (such as using a home-test kit), by a laboratory that is compatible with the Clinical Laboratory Improvement Amendment, using an FDA-approved test, using an unregulated test, etc. Moreover, a medical test may include an in vitro diagnostic test, such as: a blood test (e.g., a biochemical test a metabolic test, a molecular test and/or cellular analysis), a non-invasive radiology test (such as a medical test based on a magnetic resonance or MR technique, an X-ray technique, ultrasound, etc.), a non-destructive medical test, a destructive medical test, etc. For example, a molecular test may include protein analysis, genetic testing (such as DNA testing, RNA testing, gene expression, epigenetic testing, etc.), etc. Furthermore, the medical testing may be performed on a biological sample, such as: blood, urine, stool, spit, sputum, etc. Note that a medical test may, in general, be used to diagnosis a trait or a condition (such as the presence of a disease) and/or may be used to guide treatment. Notably, the system may determine a diagnosis and/or may select a treatment by comparing one or more test results to a set of diagnostic criteria (such as one or more symptoms, vital signs, additional test results from other medical tests, etc. that are associated with a trait or a condition) and/or a set of treatment protocols (such as one or more medical procedures, pharmaceuticals, etc., as well as an order for their use when treating a trait or a condition).

Moreover, in the discussion that follows, electronic devices and/or components in a system that includes the computer system may communicate using a wide variety of communication protocols. For example, the communication may involve wired or wireless communication. Consequently, the communication protocols may include: an Institute of Electrical and Electronics Engineers (IEEE) 802.11 standard (which is sometimes referred to as 'Wi-Fi®,' from the Wi-Fi Alliance of Austin, Tex.), Bluetooth® (from the Bluetooth Special Interest Group of Kirkland, Wash.), another type of wireless interface (such as another wireless-local-area-network interface), a cellular-telephone communication protocol (e.g., a 3G/4G/5G communication protocol, such as UMTS, LTE), an IEEE 802.3 standard (which is sometimes referred to as 'Ethernet'), etc. In the discussion that follows, Ethernet and Wi-Fi and/or a cellular telephone communication protocol are used as illustrative examples.

Communication among electronic devices is shown in FIG. 1, which presents a block diagram illustrating an example of a system 100 that iteratively performs medical tests and/or that orders medical tests. Notably, system 100 includes a medical laboratory 106, a storage repository 108, one or more electronic devices 110 (such as cellular telephones or portable electronic devices, computers, etc.), optional base station 112 in cellular-telephone network 114, optional access point 116, and computer system 118 (which are sometimes collectively referred to as 'components' in system 100). Moreover, computer system 118 may include: a set of medical knowledge 120 (such as available medical tests, which may be stored in memory or a computer-readable medium, and which may include a 'biovault'), a ranking engine (or module) 122, an analysis engine (or module) 124 and a communication engine (or module) 126. In some embodiments, the set of medical knowledge 120 includes a block chain, i.e., a distributed data structure or database that maintains a continuously growing list of records (with data, individual transactions, the results of any blockchain executables and/or programs, as well as time-stamps and links to one or more previous blocks) secured from tampering and revision, so that a history of updates and changes to the medical tests and knowledge can be maintained. Therefore, changes to the set of medical knowledge 120 may be appended to the existing set of medical knowledge 120.

Note that components in system 100 may communicate with each other via a network 128, such as the Internet, a cellular-telephone network and/or a wireless local area network (WLAN). In embodiments where the communication involves wireless communication, the wireless communication includes: transmitting advertising frames on wireless channels, detecting another component in system 100 by scanning wireless channels, establishing connections (for example, by transmitting association requests), and/or transmitting and receiving packets (which may include information for inclusion in the set of medical knowledge 120, requests for access to information in the set of medical knowledge 120, notifications, etc.).

Moreover, as described further below with reference to FIG. 9, electronic devices 110, optional base station 112, optional access point 116 and computer system 118 may include subsystems, such as a networking subsystem, a memory subsystem and a processor subsystem. In addition, electronic devices 110, optional base station 112, optional access point 116 and computer system 118 may include radios 130 in the networking subsystems. More generally, the components can include (or can be included within) any electronic devices with the networking subsystems that enable these components to communicate with each other. Note that wireless communication can comprise transmitting advertisements on wireless channels to enable a pair of components to make initial contact or detect each other, followed by exchanging subsequent data/management frames (such as association requests and responses) to establish a connection, configure security options (e.g., Internet Protocol Security), transmit and receive packets or frames via the connection, etc.

Moreover, as can be seen in FIG. 1, wireless signals 132 (represented by jagged lines) are transmitted by radios 130 in the components. For example, radio 130-1 in electronic device 110-1 may transmit information (such as packets) using wireless signals. These wireless signals may be received by radios 130 in one or more of the other components, such as by optional base station 112 or optional access point 116. This may allow electronic device 110-1 to communicate information to optional base station 112 or optional access point 116, and thus, to computer system 118.

In the described embodiments, processing a packet or frame in a component may include: receiving the wireless signals with the packet or frame; decoding/extracting the packet or frame from the received wireless signals to acquire the packet or frame; and processing the packet or frame to determine information contained in the packet or frame (such as information for inclusion in the set of medical knowledge 120, a request or query, an ordered medical test, a notification, etc.).

Note that the communication between at least any two of the components in system 100 may be characterized by one or more of a variety of performance metrics, such as: a received signal strength indication (RSSI), a data rate, a data rate for successful communication (which is sometimes referred to as a 'throughput'), an error rate (such as a retry or resend rate), a mean-square error of equalized signals relative to an equalization target, intersymbol interference, multipath interference, a signal-to-noise ratio, a width of an eye pattern, a ratio of number of bytes successfully communicated during a time interval (such as 1-10 s) to an estimated maximum number of bytes that can be communicated in the time interval (the latter of which is sometimes referred to as the 'capacity' of a communication channel or link), and/or a ratio of an actual data rate to an estimated data rate (which is sometimes referred to as 'utilization').

Figure 2:
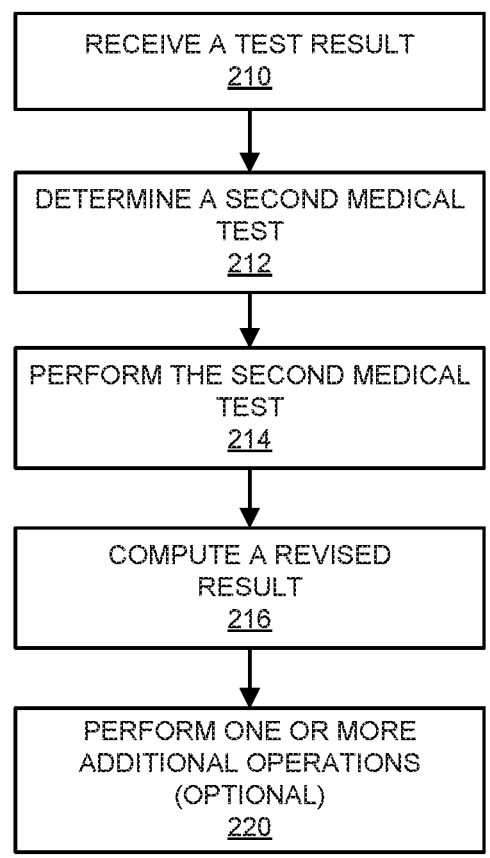
FIG. 2 is a flow diagram illustrating an example method for iteratively performing medical testing in accordance with some embodiments.

As described further below with reference to FIGS. 2 and 3, during the first group of embodiments of the testing technique computer system 118 may iteratively perform medical testing. Notably, communication engine 126 may receive, via network 128, a test result of a medical test performed on a biological sample associated with an individual (such as a patient or a subject), where the test result has an initial uncertainty (such as an initial sensitivity and/or an initial specificity). For example, communication engine 126 may receive the test result from electronic device 110-1 at medical laboratory 106 and/or from electronic device 110-2, which is associated with a healthcare practitioner of the individual or a medical researcher. In some embodiments, communication engine 126 may have previously received, via network 128, an instruction to perform the medical test on the biological sample (such as from electronic device 110-2 associated with the healthcare practitioner or the medical researcher), and in response may have previously provided, via network 128, the instruction to perform the medical test on the biological sample (such as to electronic device 110-1 at medical laboratory 106).

Then, analysis engine 124 may determine, based on the test result, a second medical test to perform on a second biological sample associated with the individual, where the second biological sample was acquired prior to the biological sample. For example, analysis engine 124 may use the test result and the set of medical knowledge 120 (such as medical records for the individual, medical records for other individuals, medical tests, diagnostic criteria for conditions and/or treatments or treatment protocols for the conditions) to determine the second medical test. In some embodiments, the second medical test is determined based on a hypothesis test and an associated contingency table, which includes the test result. Alternatively or additionally, as described below with reference to FIGS. 4 and 5, the second medical test may be determined based on a ranking.

Note that the second medical test may be a subset of or a superset of the medical test. Alternatively, the second medical test may be another instance of the medical test. Thus, the second medical test may be the same as or different from the medical test. In some embodiments, the determination is based on a group of biological samples that were previously acquired from the individual and that are available for additional medical testing (such as biological samples stored in storage repository 108), where the group of biological samples includes the second biological sample. Moreover, the determination may be based on how the group of biological samples were prepared prior to storage in storage repository 108. For example, portions of a blood sample may be prepared in different ways based on different types of medical tests, which may be subsequently performed. In some embodiments, a portion of the biological sample is stored in liquid nitrogen.

Moreover, note that, in some embodiments, information in the set of medical knowledge 120 is, at least in part, encrypted or securely hashed (such as using SHA-256) and stored separately from the encryption key(s) or the secure hashing function(s). For example, encrypted information and the associated public encryption keys may be stored in the set of medical knowledge 120, and the corresponding private encryption keys may be stored separately. Therefore, when computer system 118 accesses information in the set of medical knowledge 120, a security engine (not shown) may also provide access information, such as a public encryption key or information that specifies a secure hashing function.

Next, communication engine 126 may provide, via network 128, an instruction to perform the second medical test. For example, communication engine 126 may provide the instruction to electronic device 110-1 at medical laboratory 106. This instruction may include access information that specifies the second biological sample in storage repository 108, and which may include an electronic certificate or identifier that authorizes medical laboratory 106 to access at least a portion of the specified second biological sample in storage repository 108. (Thus, the second biological sample may be stored in storage repository 108. Moreover, in some embodiments, different portions of the second biological sample may be stored in different freezers, so that the portions can be accessed randomly to avoid thermal cycling the entire second biological sample.) Alternatively, communication engine 126 may provide, via network 128, another instruction to electronic device 110-3 at storage repository 108. This other instruction may specify the second biological sample in storage repository 108, and may instruct storage repository 108 to provide at least a portion of the second biological sample to medical laboratory 106, so that medical laboratory 106 can perform the second medical test.

After performing the second medical test, electronic device 110-1 may provide, via network 128, a second test result of the second medical test to communication engine 126. Moreover, after receiving the second medical test, analysis engine 124 may compute a revised result for the medical test based on the test result and the second test result, where the revised result has a second uncertainty that is less than the initial uncertainty. Thus, the revised result may have a second sensitivity and/or a second specificity, which, respectively, may be greater than the initial sensitivity and/or the initial specificity.

In some embodiments, communication engine 126 provide, via network 128, the revised result. For example, communication engine 126 may provide the revised result to electronic device 110-2 associated with the healthcare practitioner or the medical researcher.

Alternatively or additionally, based on the revised result and, optionally, set of medical knowledge 120, analysis engine 124 may determine a diagnosis and/or a treatment for a condition of the individual when the second uncertainty is less than a threshold. For example, the diagnosis and/or the treatment may be determined when the second sensitivity and/or the second specificity is greater than 75, 85, 95 or 99%. More generally, analysis engine 124 may determine a diagnosis and/or a treatment for a condition of the individual based on one or more quality metrics (such as a convergence criterion, a confidence interval or an accuracy of the revised test result). In some embodiments, the revised test result is also determined based on test results for the medical test and/or the second medical test for other individuals, which may be included in the set of medical knowledge 120.

Note that computer system 118 may, one or more times, iteratively repeat at least some of the aforementioned operations. For example, the revised result may be computed using a temporal sequence of biological samples that were and/or that are acquired over a time interval (such as a time interval that is characteristic of the onset or progression of the condition). Thus, the second medical test may be performed on the sequence of biological samples, which were either previously acquired at one or more previous times (i.e., retrospective medical testing) and stored in storage repository 108 and/or which are subsequently acquired at one or more future times.

While the preceding discussion used analysis engine 124 determining the second medical test as an illustration of the testing technique, in other embodiments computer system 118 may present a group of potential medical tests (which may be identified by analysis engine 124 based on the test result and/or the set of medical knowledge 120) to a user (such as a healthcare provider). For example, communication engine 126 may provide, via network 128, information that specifies a user interface to electronic device 110-2. When displayed by electronic device 110-2, the user interface may include user-interface icons associated with the group of potential medical tests. By activating one of the user-interface icons, the user may select one of the group of potential medical tests as the second medical test. (Thus, the second medical test may be specified by the user using 'one click.') More generally, user-interface activity (such as a voice command) may be used to select the second medical test. After the user selection, electronic device 110-2 may provide, via network 128, information to communication engine 126 which specifies the selected second medical test. In response, computer system 118 may perform the second medical test and/or other operations in the testing technique, as described previously.

During the second group of embodiments, computer system 118 may order a medical test on a set of biological samples. Notably, analysis engine 124 may: perform analysis of current medical information, query a data structure or a database for a set of medical tests (where the set of medical tests may be determined or identified based on the analysis of the current medical information and any available historical information), rank, using ranking engine 122, medical tests in the set of medical tests based on a marginal information value to be captured from each medical test, request one or more of the highest-ranking medical tests based on the current medical information, locate a biological sample, provide, via communication engine 126, instructions to ship the biological sample to a testing facility, receive, via the communication engine 126, test results of the medical test from the testing facility, and/or record the test results in a data structure or a database.

As illustrated below with reference to FIGS. 6 and 7, during a third group of embodiments, computer system 118 may perform a medical test. Notably, computer system 118 may store a biological sample associated with a biological lifeform in a storage repository (e.g., in cryogenic storage), such as storage repository 108. Then, computer system 118 may perform one or more MR measurements on at least a portion of the biological life form using an MR measurement device, which may be located in medical laboratory 106. For example, computer system 118 may instruct medical laboratory 106 to perform the one or more MR measurements. Note that the MR measurement device may include an MR scanner. Alternatively, the MR measurement device may include a magnet that generates an external magnetic field that polarizes at least the portion of the biological lifeform, a transmission coil that applies an RF sequence to at least the portion of the biological lifeform, and an RF coil and/or a non-inductive sensor to perform the one or more MR measurements.

Moreover, computer system 118 may quantitatively simulate an MR response of at least the portion of the biological life form, and may compare the one or more MR measurements and the quantitative simulation to obtain a first test result. Next, computer system 118 may determine one or more additional medical tests to perform that can improve an accuracy of the first test result. Furthermore, computer system 118 may access the biological sample in the storage repository to obtain at least a second portion of the biological sample, and may perform the one or more additional medical tests on at least the second portion of the biological sample to obtain one or more additional test results. For example, computer system 118 may instruct medical laboratory 106 to perform the one or more additional medical tests.

Additionally, computer system 118 may compute a second test result based at least in part on the first test result and the one or more additional test results, where the second test result has an improved accuracy relative to the first test result.

In these ways, computer system 118 may dynamically perform medical testing, which may facilitate iterative or active learning. These approaches may improve patient outcomes and may reduce medical costs.

Note that the testing technique may be used to apply medical knowledge in conjunction with a wide variety of non-invasive measurement techniques. In some embodiments, the medical test includes one or more MR techniques, such as: magnetic-resonance imaging (MRI), magnetic-resonance spectroscopy (MRS), another MR technique, computed tomography, ultrasound imaging, X-ray imaging, positron emission spectroscopy, electron spin resonance, optical/infrared spectroscopy (e.g., to determine a complex index of refraction at one or more wavelengths), an electrical measurement (such as an electrocardiogram, an electromyogram, an electroencephalogram, etc.), proton beam, photoacoustic imaging, other non-destructive measurements (such as radar or millimeter-wave scanning), activity or behavior data for a biological organism (such as data capture using a wearable electronic device), measurements performed by nano particles in the biological sample, chemical composition of fluids (such as blood) measured at arbitrary locations in the biological organism non-destructively or by drawing a blood sample (e.g., using microfluidics), height, weight, a vital sign (pulse, respiration, temperature, blood pressure, etc.), genetic or genomic information (such as sequencing, next-generation sequencing, RNA sequencing, epigenetic information, etc.), quantitative tensor field maps, medical images, blood or lab tests, microbiome analysis, urine analysis, stool analysis, thermal-imaging readings, optical images, body impedance, biopsies, another quantitative or qualitative characteristic or property of the biological sample, etc.

Moreover, the MR technique may include quantitative analysis of MR scans such as MR fingerprints of the biological sample that are magnetic-field invariant (which are sometimes referred to as 'magnetic-field-invariant MR signatures' or 'invariant MR signatures'). The invariant MR signatures may describe the dynamic MR responses of voxels at 3D positions in the one or more biological samples at arbitrary magnetic-field strengths. Moreover, the invariant MR signatures may be independent of the MR scanners, as well as the specific scanning instructions (e.g., magnetic-field strengths and/or pulse sequences), used to acquire MR signals in a variation on MRF (which is sometimes referred to as 'quantitative MRF' or QMR-X) that were then used to determine the invariant MR signatures. An invariant MR signature may be determined by iteratively converging MR signals of one or more types of nuclei in the biological sample, which were acquired by an MR scanner based on scanning instructions, with simulated MR signals (which are sometimes referred to as calculated MR signals or estimated MR signals) for the biological sample that are generated using an MR model and the scanning instructions.

Furthermore, the MR technique may include: MRI, MRS, magnetic-resonance spectral imaging (MRSI), magnetic-resonance thermometry (MRT), magnetic-resonance elastography (MRE), MR fingerprinting (MRF), magnetic-field relaxometry, diffusion-tensor imaging and/or another MR technique (such as functional MRI, metabolic imaging, molecular imaging, blood-flow imaging, etc.). Note that these MR techniques are each a form of quantitative tensor-field mapping.

Notably, 'MRI' should be understood to include generating images (such as 2D slices) or maps of internal structure in a sample (such as anatomical structure in a biological sample, e.g., a tissue sample or a patient) based on the dynamic response of a type of nuclear spin (such protons or the isotope $^1H$) in the presence of a magnetic field, such as a non-uniform or spatially varying external magnetic field (e.g., an external magnetic field with a well-defined spatial gradient). In addition, MRS should be understood to include determining chemical composition or morphology of a sample (such as a biological sample) based on the dynamic response of multiple types of nuclear spins (other than or in addition to $^1H$) in the presence of a magnetic field, such as a uniform external magnetic field.

Moreover, 'MRSI' should be understood to include generating images or maps of internal structure and/or chemical composition or morphology in a sample using MRS in the presence of a magnetic field, such as a non-uniform or spatially varying external magnetic field. For example, in MRSI the measured dynamic response of other nuclei in addition to $^1H$ are often used to generate images of the chemical composition or the morphology of different types of tissue and the internal anatomy of the biological sample.

Furthermore, in contrast with existing approaches to MRI or MRSI that usually provide qualitative or 'weighted' measurements of a limited set of properties, 'MRF' should be understood to include quantitative measurements of the properties of a sample by acquiring signals representing a dynamic or time-dependent magnetization or MR trajectory (such as in k-space) from different materials in a sample using a pseudorandom pulse sequence. Notably, instead of using repeated, serial acquisition of data to characterize individual model parameters that are of interest, in MRF signals from different materials or tissues are often acquired using a pseudorandom pulse sequence to determine a unique signal or 'fingerprint' (e.g., a time-dependent magnetization or MR trajectory). The resulting unique fingerprint of the sample is, in general, a function of multiple material properties under investigation. For example, MRF can provide high-quality quantitative maps of: a spin-lattice relaxation time $T_1$ (which is the time constant associated with the loss of signal intensity as components of the nuclear-spin magnetization vector relax to be parallel with the direction of an external magnetic field), a spin-spin relaxation time $T_2$ (which is the time constant associated with broadening of the signal during relaxation of components of the nuclear-spin magnetization vector perpendicular to the direction of the external magnetic field), proton density (and, more generally, the densities of one or more type of nuclei) and diffusion (such as components in a diffusion tensor).

Note that 'magnetic-field relaxometry' (such as $B_0$ relaxometry with the addition of a magnetic-field sweep) may involve acquiring MR images at different magnetic-field strengths. These measurements may be performed on the fly or dynamically (as opposed to performing measurements at a particular magnetic-field strength and subsequently cycling back to a nominal magnetic-field strength during readout, i.e., a quasi-static magnetic-field strength). For example, the measurements may be performed using un-tuned radio-frequency (RF) coils or a magnetometer so that measurements at the different magnetic-field strengths can be performed in significantly less time.

Additionally, 'MRE' should be understood to include measuring the stiffness of a sample using MRI by sending mechanical waves (such as sheer waves) through a sample, acquiring images of the propagation of the shear waves, and processing the images of the shear waves to produce a quantitative mapping of the sample stiffness (which are sometimes referred to as 'elastograms') and/or mechanical properties (such as rigidity, density, tensile strength, etc.).

Moreover, 'MRT' should be understood to include measuring maps of temperature change in a sample using MRI.

Note that a biological sample may include a tissue sample from an animal or a person (i.e., a portion of the animal or the person). For example, the tissue sample may have been previously removed from the animal or the person. In some embodiments, the tissue sample is a pathology sample, such as a biopsy sample. Thus, the tissue sample may be formalin fixed-paraffin embedded. However, in other embodiments a biological sample may be in the animal or the person (i.e., an in-vivo sample) and/or the measurement technique involves whole-body scans. Furthermore, the measurement technique may also be applied to inanimate (i.e., non-biological) samples of a wide variety of different materials. In the discussion that follows, the biological sample is taken or acquired from a person or an individual, which is used as an illustrative example.

Although we describe the network environment shown in FIG. 1 as an example, in alternative embodiments, different numbers or types of electronic devices may be present. For example, some embodiments comprise more or fewer components, a position of a component is changed and/or two or more components are combined. In some embodiments, system 100 excludes base station 112 and/or network 128. As another example, in another embodiment, different components are transmitting and/or receiving packets or frames.

We now describe embodiments of the testing technique. FIG. 2 presents a flow diagram illustrating an example method 200 for iteratively performing medical testing, which may be performed by a system (such as computer system 118 in FIG. 1). During operation, the system receives a test result (operation 210) of a medical test performed on a biological sample associated with an individual, where the test result has an initial uncertainty (such as an initial specificity and/or an initial sensitivity).

Then, the system determines, based on the test result, a second medical test (operation 212) to perform on a second biological sample associated with the individual, where the second biological sample was acquired prior to the biological sample. Note that the determination may be based on a group of biological samples that were previously acquired from the individual and that are available for additional medical testing, where the group of biological samples includes the second biological sample. Moreover, the determination may be based on how the group of biological samples were prepared prior to storage.

Furthermore, the system performs the second medical test (operation 214) on the second biological sample to obtain a second test result of the second medical test. For example, performing the second medical test may involve accessing the second biological sample in a storage repository. Alternatively or additionally, performing the second medical test may involve: providing an instruction to perform the second medical test; and receiving the second test result.

Next, the system computes a revised result (operation 216) for the medical test based on the test result and the second test result, where the revised result has a second uncertainty (such as a second specificity and/or a second sensitivity) that is less than the initial uncertainty.

In some embodiments, the system optionally performs one or more additional operations (operation 218). For example, prior to receiving the test results (operation 210), the system may receive an instruction to perform the medical test on the biological sample; and provide the instruction to perform the medical test on the biological sample. Moreover, in some embodiments, the system provides the revised result.

Furthermore, one or more additional instances or iterations of the determining (operation 212), the performing (operation 214) and the computing (operation 216) may be performed in a temporal sequence over a time interval. For example, the second biological sample may include a temporal sequence of biological samples acquired over a time interval and the second medical test may be performed on the sequence of biological samples.

Additionally, the system may determine a diagnosis for a condition of the individual based on the revised results when the second uncertainty is less than a threshold.

Figure 3:
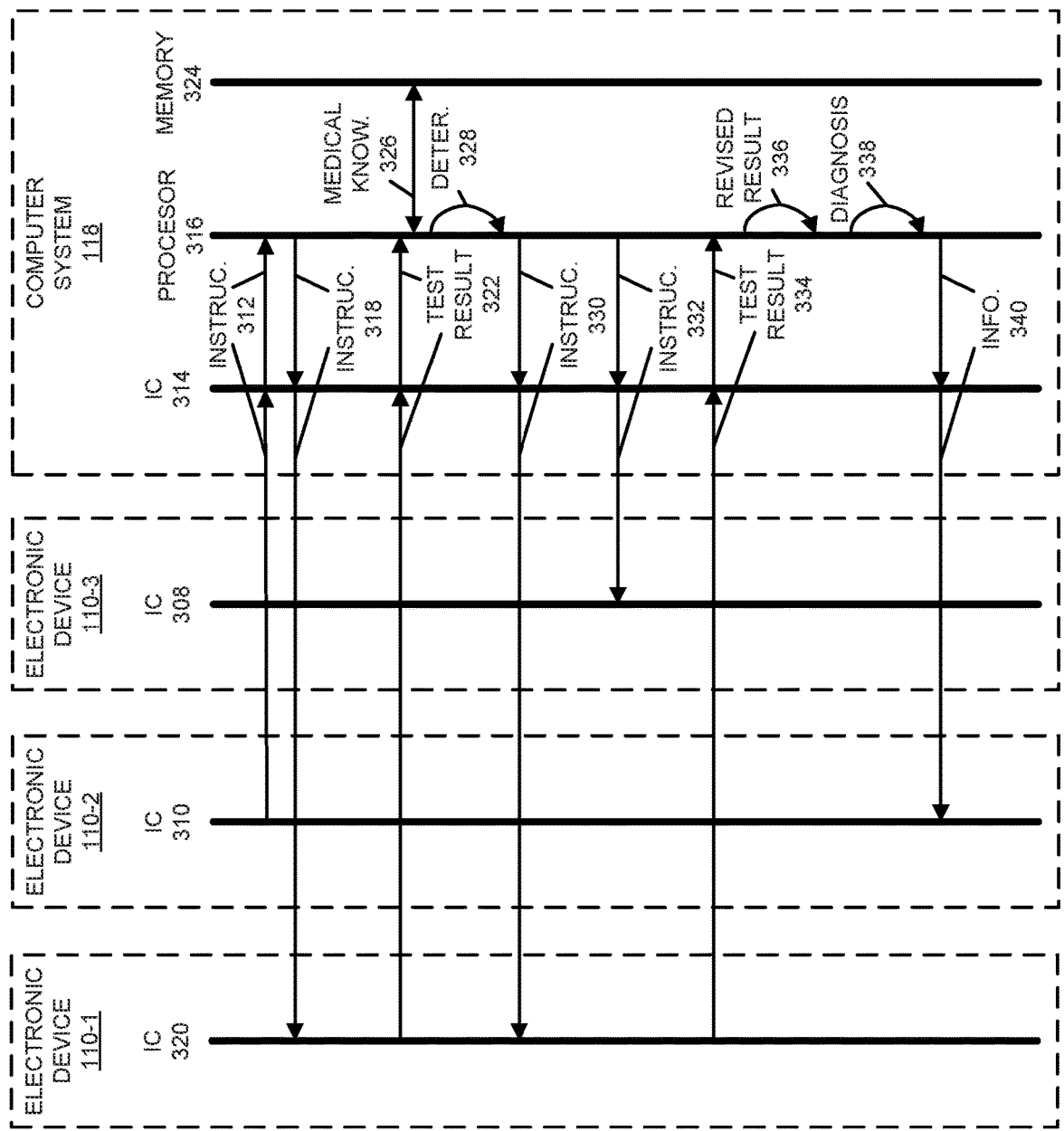
FIG. 3 is a drawing illustrating an example of communication among electronic devices in the system of FIG. 1 in accordance with an embodiment of the present disclosure.

Embodiments of the testing technique are further illustrated in FIG. 3, which presents a drawing illustrating an example of communication among components in system 100 (FIG. 1). Notably, during the testing technique, interface circuit (IC) 310 in electronic device 110-2 (which is associated with a healthcare provider) may provide, to interface circuit 314 in computer system 118, an instruction 312 to perform a medical test on a biological sample associated with an individual (and, more generally, a biological organism, which may be an animal, a person, etc.). In response, interface circuit 314 may forward instruction 312 to processor 316, which may provide, via interface circuit 314, an instruction 318 to electronic device 110-1 at medical laboratory 106 to perform the medical test on the biological sample.

After interface circuit 320 in electronic device 110-1 receives instruction 318, medical laboratory 106 may perform the medical test. Moreover, interface circuit 320 may provide, to interface circuit 314, a test result 322 of the medical test performed on the biological sample. Next, interface circuit 314 may provide test result 322 to processor 316. Processor 316 may access medical knowledge 326 in memory 324. Then, using test result 322 and medical knowledge 326, processor 316 may determine 328 a second medical test to perform on a second biological sample associated with the individual, where the second biological sample was acquired prior to the biological sample.

Next, processor 316 may provide, via interface circuit 314, instruction 330 to electronic device 110-1 to perform the second medical test on the second medical sample, and may provide, via interface circuit 314, instruction 332 to interface circuit 308 in electronic device 110-3 at storage repository 108 to provide the second medical sample to medical laboratory 106.

After performing the second medical test, interface circuit 320 may provide a test result 334 of the second medical test to interface circuit 314, which then provides test result 334 to processor 316. Furthermore, processor 316 may compute a revised result 336 for the medical test based on test results 322 and 336, where revised result 336 has an uncertainty that is less than an uncertainty of test result 322.

In some embodiments, processor 316 determines a diagnosis 338 for a condition of the individual based, at least in part, on revised results 336 when the uncertainty of test result 336 is less than a threshold. (Note that the uncertainty of test result 322 may be greater than the threshold.) Moreover, processor 316 may provide, via interface circuit 314, information 340 (including revised results 336 and/or diagnosis 338) to interface circuit 310 in electronic device 110-2.

Figure 4:
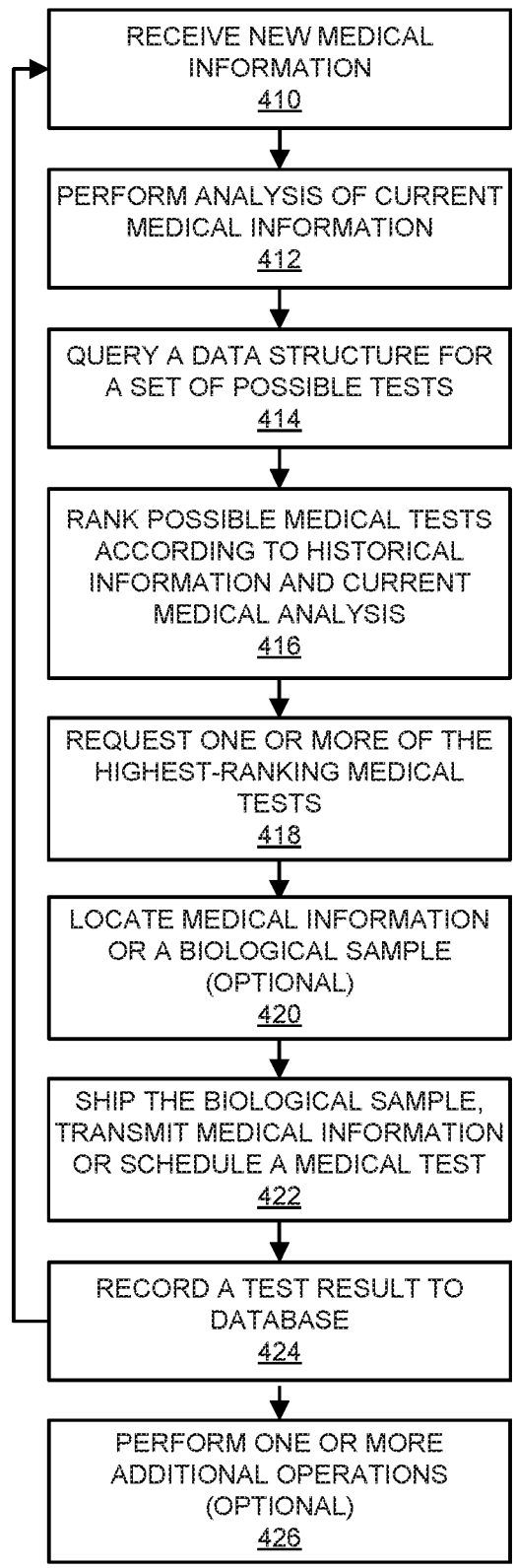
FIG. 4 is a flow diagram illustrating an example method for ordering medical tests on biological samples in accordance with an embodiment of the present disclosure.

FIG. 4 presents a flow diagram illustrating an example method 400 for ordering medical tests on biological samples, which may be performed by a system (such as computer system 118 in FIG. 1). During operation, the system may perform the operations of: receiving new medical information (operation 410), performing analysis of current medical information (operation 412), querying a data structure or a database for a set of medical tests (operation 414), ranking possible medical tests according to historical information and current medical analysis (operation 416), requesting one or more of the highest-ranking medical tests (such as the top one, three or ten medical tests) (operation 418), and recording the test result to a data structure or a database (operation 424). In some embodiments, the computer system performed one or more additional optional operations, including: locating medical information or biological sample (operation 420), arranging shipment of a biological sample or transmission of medical information or the scheduling of a medical test (operation 422), and/or performing one or more additional operations (operation 426).

During operation 410, the system may receive new medical information. For example, the system may receive: a new test or assay result (possibly from a previous instance or iteration of method 400), new information about a patient or a relative of a patient (e.g., new or additional family history information). This new information may be used in the analysis of current medical information in operation 412.

Notably, during operation 412, the system may perform analysis of current medical information. This may include assessing current test results (e.g., from a current examination or test result that was recently or just performed and/or the new information received in operation 410). Then, the system may determine a current state of information or a diagnosis for a patient. Note that a healthcare practitioner may perform operation 412 or it may be performed by a software program or program module that captures the current information and that provides a summary of probabilities based on, e.g., Bayesian statistics. For example, the system may compare current information and symptoms with a computed population from a biovault, a data structure or a database (such as the set of medical knowledge 120 in FIG. 1). This comparison may indicate that a patient has a 60% chance of having condition A and a 40% chance of having condition B.

Then, during operation 414, the system may query the data structure or database for a set of medical tests or assays, and may determine which test results can be performed with the information and biological samples that are available. For example, if a patient history includes MRI images, monthly blood samples, and quarterly tissue biopsies of cancer, a sample set of tests can include: MRI image analysis over time of a cancerous tumor, tissue biopsy analysis over time to measure growth of a cancerous tumor, and/or measurements of genetic fragments in blood samples (such as a liquid biopsy) over time to estimate how fast the tumor cells are mutating. This set of tests can be constantly updated as new research is released.

The incorporation of new research and tests and assays into method 400 may enable a previous assay that tested a blood sample for a biomarker to be updated with new tests, methodologies and procedures (or it may be performed again to verify results). Alternatively or additionally, a new test may be performed on historical samples to detect when an issue or a condition (such as a disease) first appeared, and to estimate the progress of the condition. For example, by measuring the genetic fragments in a set of historical blood samples for a patient who was recently diagnosed with cancer, the system may assist a doctor in identifying the rate of growth of that cancer, the age of the cancer, the effectiveness of a treatment over time (e.g., a cancer shrinking in size or disappearing over time post treatment, and traces disappear from subsequent blood samples post treatment), etc.

In another embodiment, the system may suggest a set of assays to run on the available biological samples from an individual, and the assays may be selected based upon information available to the system in order to identify a heart attack pattern based on a historical EKG or a real-time EKG. Moreover, the system may use knowledge of the blood drawn when the heart attack symptoms appeared, and may recommend an order to assay blood levels for the enzyme creatine phosphokinase (CPK) (which is also called creatine kinase (CK) and proteins proponin I (TnI) and troponin T (TnT). This may allow the assay to assess information on current and previous heart attacks suffered by a patient and provide a very clear picture to a healthcare practitioner.

Moreover, during operation 416, the system may rank possible medical tests according to historical information and current medical analysis may determine one or more medical tests that may provide value for a healthcare practitioner and a patient. In order to generate one or more rankings of assays, note that the current state of medical information or analysis or diagnosis from operation 412 may be used in operation 416 in conjunction with the set of possible medical tests or assays determined in operation 414. These rankings may be used as a recommendation or scoring for which assays to order on behalf of a patient. In some embodiments, the ranking is based on one or more metrics or dimensions. For example, a marginal information-value calculation may be performed relative to the current state of medical information from operation 412. This calculation may depend on the current health status of a patient. In determining the marginal-information value of an additional assay that may be performed on an archived biological sample, or in some cases the re-analysis of raw data captured from a historical assay, the system may apply one or more constraints, including: estimated patient outcome, estimated cost, an accuracy or uncertainty of a diagnosis, etc.

The amount of marginal information improvement available from a medical test may be the sole ranking criterion, and the system may determine this using a Bayesian filter or Bayesian decision tree. (However, a wide variety of supervised and unsupervised learning techniques may be used.) For example, if a patient has a 60% chance of having condition A or a 40% chance of having condition B, and a medical test operating on their current and historical blood samples will increase the certainty of the Bayesian filter to 90%, then that medical test may be ranked highly. However, another ranking technique may be used, and it may be used independently or in conjunction with the Bayesian filter. Notably, the system may apply weights based on the seriousness of condition A and condition B, such as if Condition A is cosmetic and condition B is fatal. In this example, it may be valuable (for patient comfort and peace of mind) to know for certain that the patient did not have the fatal condition B. Therefore, while the marginal information value of a blood test performed on the current and historical blood samples of the patient may provide good marginal information, a biopsy test with 99% accuracy may be ranked higher because condition B is weighted more heavily. Note that additional weights and/or tuning may be applied, such as costs. This may enable a patient or a doctor to specify that any medical tests that cost below a certain amount and that provide at least some marginal information value improvement are to be automatically approved, regardless of their rank (i.e., a lower cost may improve the rank position).

Furthermore, re-analysis of raw data may be used in addition to archived biological samples because it is possible that a previous diagnosis may be incorrect (such as because of a human radiologist or a laboratory mix up) and may be in conflict with the results of a Bayesian filter or decision tree. Other forms of raw data that can be re-analyzed may include spectral data from mass spectrometry, NMR, etc., using newer versions of data analysis tools or techniques with larger data structures or databases of examples for analysis with Bayesian or other artificial intelligence tools (such as a neural network).

For example, repeating a medical test again, before a particularly serious treatment or surgery, can provide additional confirmation that the treatment or surgery is necessary, especially if it entails risk. In some embodiments, a different laboratory or a set of laboratories may be used to provide diversity for a second opinion and to make sure that biological samples were not mixed up or tainted and that the medical test was performed properly. The assurance provided to healthcare practitioners (who wish to avoid malpractice litigation) and patients (who are often anxious before major medical procedures), and the reduction of mistakes may provide improved experiences and outcomes for all involved in the healthcare industry.

Note that, in the same way a human radiologist may make an incorrect diagnosis. For example, a machine-based approach may make mistakes using incorrect (or not enough data) to form a classifier (such as a Support Vector Machine), a decision tree or a Bayesian filter, so adding additional information before re-analyzing the data may provide a better idea of what medical tests may be ranked higher than others. Moreover, the additional medical test can be performed without even needing to contact the patient (or a doctor or another medical professional) to take a biological sample or another measurement (e.g., by using a previously acquired biological sample). Therefore, the testing technique may provide higher information quality and a second opinion potentially faster and at a potentially lower cost. Furthermore, the destructive nature of medical tests can be factored in (e.g., whether or not the medical test will destroy or contaminate a biological sample or permanently alter the biological sample, whether or not the medical test is non-destructive, etc.). If a medical test is important enough (e.g., a life or death situation rather than a vanity metric), the destructive medical test may be ranked highly based on the additional information the medical test can provide to the Bayesian decision tree or to a healthcare practitioner.

In an alternative embodiment, in the absence of a Bayesian decision tree or Bayesian filter, or in addition to such a model, decision tree or filter as would be known to one skilled in the art, a motivation for ranking a medical test above another would be conflicting evidence and the ability of a medical test to resolve such conflicting evidence. For example, the system may order an additional test if there is a large body of specific evidence that points toward a specific diagnosis with the exception of a single piece of evidence that seems inconsistent based on the instincts of a doctor or based on models of human physiology and pathology, and ordering a medical test or a re-analysis of existing test results may help resolve the information conflict and may provide reduced uncertainty in a diagnosis, treatment and/or to validate a medical model or simulation. Moreover, if the system can accurately model physiology, the rankings or predictions may be based on the model, and the previous historical examples may not be as relevant or may be used to further reinforce the decisions made by a technique such as: a Bayesian decision tree, a Bayesian filter, CART, SVM, Lasso, a supervised-learning technique and/or an artificial intelligence technique.

Additionally, during operation 418, the system may request one or more of the highest-ranking medical tests. This may include requesting one or more medical tests that are ranked above a threshold in operation 416. Operation 418 may be manually performed by a healthcare practitioner (such as a doctor or nurse or nurse practitioner), by the patient themselves (through a consumer service), and/or by an automated system that is analyzing medical data as new data and medical tests become available. Note that the system may have an opt-in or an opt-out approval by doctors and patients. As noted previously, operation 418 may also request any medical test below a predetermined cost threshold, where the cost threshold may be decided or specified by a patient, a medical facility, a doctor, an insurance company, a pharmaceutical company, a government agency and/or another entity.

The second medical test may be pre-approved by a healthcare practitioner as safe or low risk, or pre-approved by a patient or health-insurance provider as being low cost and automatically approved. This may be the case if there is any improvement in the accuracy of the analysis (thus, the 'opt-in' by the patient or the payer, and 'opt-approval' by a healthcare practitioner may be optional). The system may also include opting out of automatic medical tests for patients with a condition that can complicate the second medical test (e.g., penicillin allergy or other factor that might limit the effectiveness of a medical test). Moreover, the system may also factor in the time needed for a medical test (e.g., immediate test results, test results in 6 hours, test results in 6 weeks, etc.). Additionally, test results may be subsidized by a research study by a university or a corporation, and thus more likely to be approved by the system because of the reduced cost. Furthermore, if the medical test is low risk, it may be determined to be a good experimental candidate for a patient.

In some embodiments, the ordering of the assay or medical test may not require the approval of a provider, but there may be an opt-in or a configuration operation in which a patient and/or a service provider is allowed to provide configuration instructions for which assays are allowed to be selected and/or configured. Alternatively, a doctor (or a patient) may order a set of assays with 'one-click' in a user interface or a single voice command to the system.

In optional operation 420, when locating medical information or a biological sample, the system may locate an electronic medical record or a biological sample in storage (such as blood, saliva, hair, sweat, urine, tears, mucus, stomach acid, stool, cerebral spinal fluid, a tissue sample, another tissue sample or a fluid sample, and/or any other suitable sample). The accessed information may include diagnoses, and/or raw bioinformatics information, such as: test results from genetic testing, cell free DNA/RNA, epigenetic testing, transcriotomic testing, proteomic testing, lipidomic testing, metabolomic testing, microbiomic testing, psychiatric testing personality testing, and/or another suitable medical test.

Moreover, during optional operation 422, when arranging shipment of a biological sample, transmission of medical information or the scheduling of a medical test, the system can locate (via a human operator or a robotic operator) medical records or marked biological samples in storage (e.g., test tube vials of blood stored in cold storage or electronic medical records of an MR scan) and may either arrange for shipping or transmission of the biological samples or medical records to a testing or analysis facility (such as a medical laboratory). Alternatively, a robotic operator may package biological samples for transport to a medical testing facility, including: addressing, labeling, specifying time sensitivity, handling, scheduling of delivery/pickup/secure handoff, etc. Similarly, for electronic medical records, a software program (which is described in more detail below) may be used to automatically (and securely) transmit or grant access to a testing or analysis facility, such that a medical test or analysis can be performed and test results can be returned.

In some embodiments, a patient can be scheduled for an MR scan. For example, the system may automatically access their schedule and the schedule of an MR scanning facility in order to schedule the MR scan for that subject or patient. The system may also anonymously evaluate the relative seriousness of the patient's condition and the relative urgency of the medical test relative to other patients, and may request that other patients let someone with a more serious condition be scheduled ahead of them, which can have a positive effect on patients in a medical community by allowing them to help each other and, therefore, feeling like others will also help them.

For example, in some embodiments, a medical test order processing subsystem or program module in the system may order or schedules tests on behalf of a user of the system. The medical test order processing subsystem may include a robot logistics system to select a biological sample for shipping, and a packaging and labeling subsystem may ship a biological sample to a testing facility. Alternatively, the medical test order processing subsystem may be an electronic file transfer service that can send electronic data to a third party for reprocessing, simulation, analysis or other information processing. In another embodiment, the medical test order processing subsystem includes a scheduling agent that can connect the calendars of a patient and/or a medical testing facility to schedule a medical test such as a blood test, an imaging test (such as an X-Ray, an MR scan, a CT) at a time that works for the patient and the testing facility. The medical test order processing subsystem may also factor in the seriousness of the condition of a patient or subject and may prioritize scheduling or shipping of biological samples for patients with more serious conditions or test results, in order to get these patients or subjects their test results faster and to reduce the stress of waiting for the test results. In some embodiments, the medical test order processing subsystem includes a program module running on an operating system, stored in memory and executed by a processing subsystem.

During optional operation 424, the system may record the test result into a data structure or a database. In some embodiments, the system may capture the test results as soon as they come in. Note that medical test or assay results can be received by mail and either scanned in, analyzed with optical character recognition (OCR) and/or manually entered. Alternatively, medical test or assay results may be received from an API, received in response to an API query, received via email, etc. The test results may be recorded in a data structure or a database and encrypted. Operation 424 may also include storing biological samples or returning previously tested samples to storage, such as a storage repository.

Moreover, during optional operation 426, the system may perform one or more additional operations, such as: altering caretakers or family members of test results, sending out educational information about conditions and medical tests on historical data, new tests that have become available, encrypting, securing, or obfuscating information in the data structure or database as needed to enhance security, and/or sending push notifications to a patient, a doctor, a medical scheduling assistant, or another person.

As new information from the test results is received during operation 424, the system may repeat operation 410 in a loop to iterate and order new medical tests until a diagnosis is returned. However, for each additional diagnosis, simulation, and treatment, the system may continuously order new medical tests and may continuously improve the medical knowledge: available to the system, the healthcare practitioners that may be using the system, and/or the patients that may be using the system as a consumer application. In a sense, the system may be a continuous-learning feedback system that orders medical test on behalf of patients and healthcare practitioners alike, and which may greatly improve the speed and quality of a healthcare system, while lowering costs or increasing the cost-effectiveness of treatment.

Figure 5:
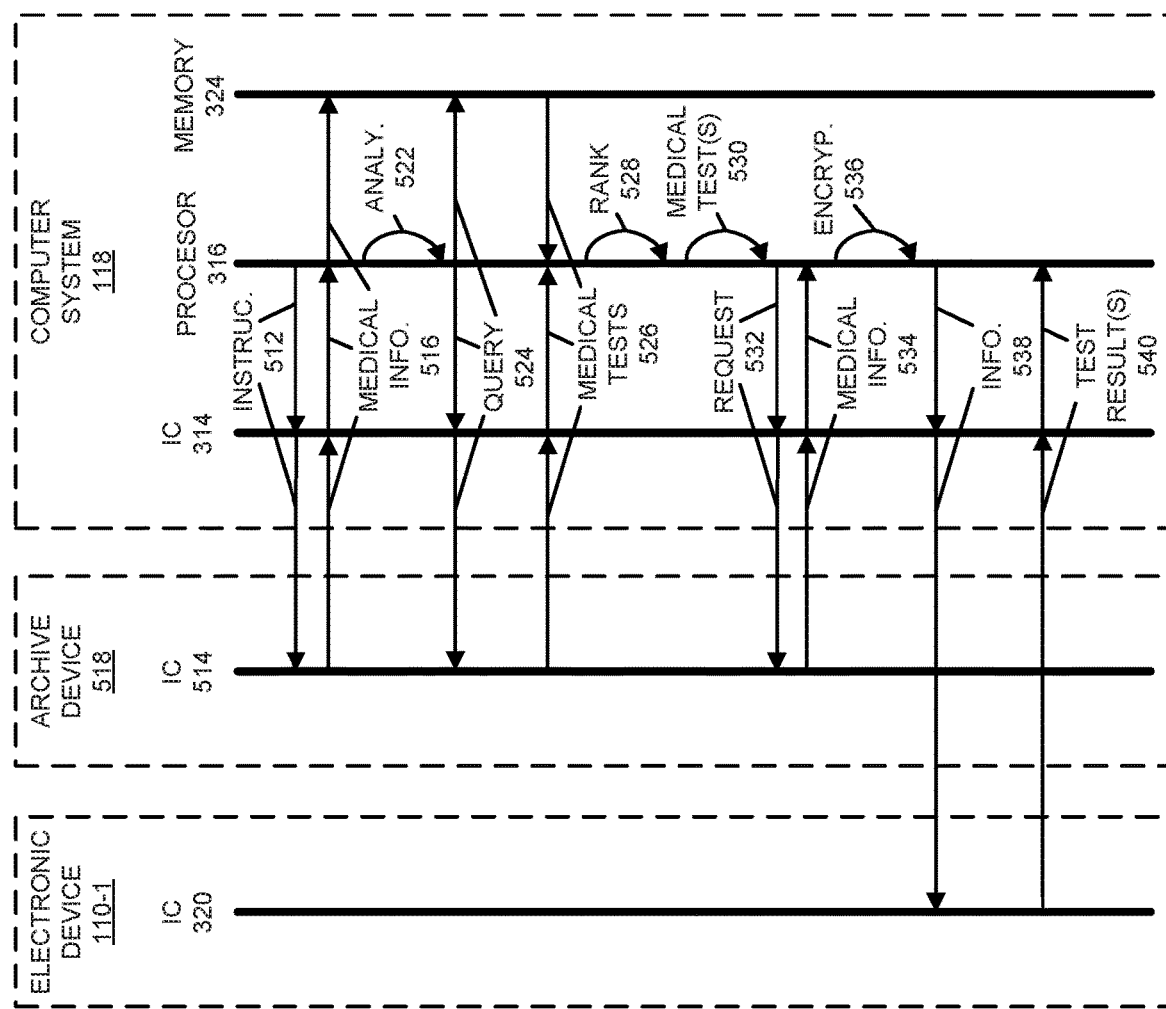
FIG. 5 is a drawing illustrating an example of communication among electronic devices in the system of FIG. 1 in accordance with an embodiment of the present disclosure.

Embodiments of the testing technique are further illustrated in FIG. 5, which presents a drawing illustrating an example of communication among components in system 100 (FIG. 1). Notably, during the testing technique, processor 316 in computer system 118 may instruct 512 interface circuit 314 in computer system 118 to access and retrieve a set of current medical information 516 from a remote archive device 518, which is then provided to memory 324 via processor 316.

Then, processor 316 may analyze 522 the available current and the historical medical information. Moreover, processor 316 may query 524 one or more data structures in archive device 518 (which may include a storage repository) and/or memory 324 to obtain a set of possible medical tests 526. Furthermore, processor 316 may rank 528 the possible medical tests 526 based on the available historical information and the current medical analysis or test results.

Next, processor 316 may select one or more medical tests 530 based on one or more selection criteria and may order the one or more medical tests 530 via interface circuit 314.

In some embodiments, processor 316 may order the one or more medical tests 530 by executing a program module that implements a medical test order processing subsystem. This program module may perform a variety of functions. For example, the medical test order processing subsystem may process requests for electronic information (such as measurements, images, quantitative measurements, previous test results, new medical tests). Moreover, the medical test order processing system may request 532 medical information from archive device 518 via interface circuit 314. In response, archive device 518 may locate the requested medical information (such as an MRI image that has been analyzed by a radiologist, so that it can be analyzed by a different radiologist for a second opinion) and archive device 518 may return the medical information 534 via interface circuits 314 and 514 to computer system 118 for subsequent processing by processor 316, which may include secure transmission (such as encryption 536) of instructions 538 to a testing or an analysis facility, such as electronic device 110-1 at medical laboratory 106.

The medical test order processing subsystem may also host information that a healthcare practitioner can access through a web browser, or that a computerized analysis tool (such as an artificial intelligence analysis program) can access via an API. Moreover, the medical test order processing subsystem may receive test result(s) 540 from a third-party testing service (such as medical laboratory 106), or an internal testing service via an API, an email, a text message, a scanned document, etc.

Note that processor 316 may optionally perform one or more additional operations. For example, processor 316 may encrypt test result(s) 540 before transmitting test result(s) 540, via interface circuit 314, to archive device 518. Archive device 518 may then record or store test result(s) 540 in a data structure or a database.

In some embodiment, the medical test order processing subsystem may process requests for biological sample testing (such as fluid samples, tissue samples, endocrine samples, etc.). Note that archive device 518 may include a robotic logistics system that can receive requests for biological samples via a network (such as network 128 in FIG. 1). Moreover, archive device 518 may use a robotic logistics system to store biological samples (such as blood and other fluids) in cold storage and/or in formalin-fixed paraffin embedded tissue. The biological samples may be labeled with names and other identifying information or may be labeled with a sample identifier for anonymity). Subsequently, archive device 518 may retrieve and convey the biological sample via a robotic courier, a conveyor system, a pneumatic tube system, a human courier and/or another suitable conveyance to a medical laboratory. For example, archive device 518 may package (in a box or secure container), preserve (with dry ice or another cooling agent) and label (with shipping information) the biological sample for shipment to a third-party facility (or an internal facility) where it can be processed by at least one third-party testing facility.

The medical test order processing subsystem may receive the test results from a third-party testing service, or an internal testing service via an API, an email, a text message, a scanned document, etc. Additionally, archive device 518 may receive a returned biological sample (if it was not destroyed during the medical testing) for continued storage, in case the biological sample needs to be tested again in the future. In some embodiments, the medical test order processing subsystem may: prepay for the medical test, pay upon receiving test results, and/or may bill for the medical test.

In some embodiments, the medical test order processing subsystem processes requests for scheduling of medical tests (such as drawing a blood sampling by a phlebotomist, imaging with an MR scanner, X-ray imaging or CT Tomography, etc.). During the scheduling, the medical test order processing system may request information from archive device 518, and in response archive device 518 may locate scheduling information for a patient, or alternatively the medical test order processing system may request scheduling information from a patient directly via email or an application. Moreover, the medical test order processing system may request scheduling information from at least one third-party testing service via email or a calendar application interface. Processor 316 may process the scheduling information (as well as information stored in the memory 324, which has been retrieved from archive device 518 and may refer to other patients, and may attempt to schedule patients with more serious medical conditions before patients with less serious medical conditions, as well as finding a time that works between the third-party testing center (or an internal testing site associated with the system) and one or more patients.

After the patient(s) go for their scheduled medical tests, the testing facilities may transmit the test results electronically to the medical test order processing subsystem, or the medical results may be entered by a medical transcriptionist, a medical professional, or a mailed document can be scanned in, and the test results can be received by the medical test order processing system. Alternatively or additionally, the medical test order processing subsystem can receive the test results from a third-party testing service or an internal testing service via an API, an email, a text message, a scanned document.

In some embodiments, as new information from the test results is received, one or more of the aforementioned operations may be repeated in a loop to iterate and order new medical tests until a diagnosis is returned. However, for each additional diagnosis, simulation, and/or treatment, the system may continuously order new medical tests and continuously improve the knowledge available to the system, the healthcare practitioners using the system, or the patients using the system as a consumer application. As noted previously, the system may be a continuous-learning feedback system that medical orders test on behalf of patients and healthcare practitioners alike (such as in an automated manner). Therefore, the system may greatly improve the speed and quality of a healthcare system, while lowering costs or increasing the cost effectiveness of treatment.

Figure 6:
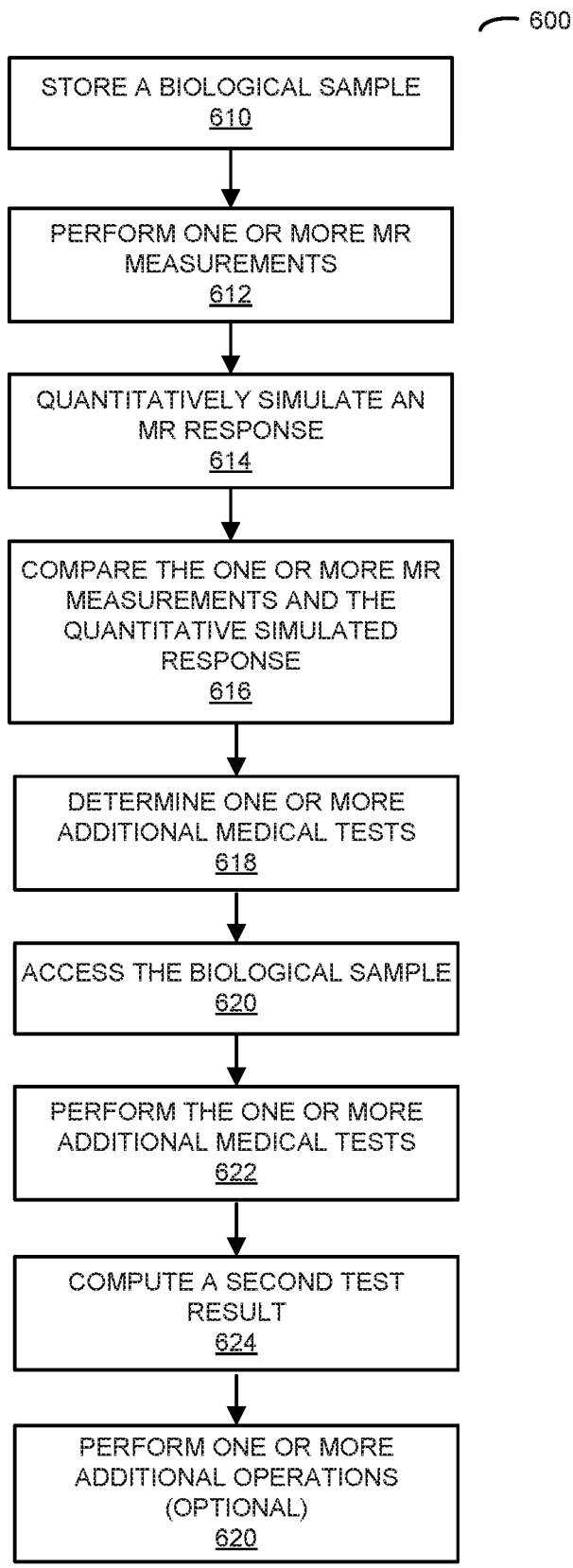
FIG. 6 is a flow diagram illustrating an example method for performing a medical test in accordance with an embodiment of the present disclosure.

FIG. 6 presents a flow diagram illustrating an example method 600 for performing a medical test, which may be performed by a system (such as computer system 118 in FIG. 1). During operation, the system may store a biological sample (operation 610) associated with a biological life form. For example, the biological sample may be stored in a repository (which is sometimes referred to as a 'storage repository'), such as a cryogenic repository. Moreover, as described further below with reference to FIG. 8, the storing may involve dividing and separately storing two or more portions of the sample. In some embodiments, storing the biological sample may involve storing a longitudinal sequence of biological samples associated with the biological life form over a time interval (such as every week, month, 3 months, 6 months, year, etc.).

Then, the system may perform one or more MR measurements (operation 612) on at least a portion of the biological life form using an MR measurement device. Moreover, the system may quantitatively simulate an MR response (operation 614) of at least the portion of the biological life form, and may compare the one or more MR measurements and the quantitative simulation (operation 616) to obtain a first test result.

In some embodiments, the quantitative simulation may involve a forward calculation based at least in part on an invariant MR signature of at least the portion of the biological sample, a pulse sequence, a magnetic-field strength, a magnetic-field gradient, magnetic-field inhomogeneities of the MR measurement device, and/or a noise characteristic of the MR measurement device. For example, the invariant MR signature may characterize an MR response of at least the portion of the biological sample to MR measurement conditions that comprise a given pulse sequence, a given magnetic-field strength and/or a given magnetic-field gradient selected from a range of pulse sequences, a range of magnetic-field strengths and/or a range of magnetic-field gradients.

Moreover, the invariant MR signature may be determined using an inverse calculation based at least in part on additional MR measurements on at least the portion of the biological sample or a different portion of the biological sample and the MR measurement conditions. The invariant MR signature may be independent of an MR measurement device used to acquire the additional MR measurements that were used to determine the invariant MR signature. For example, an invariant MR signature may include model parameters at the voxel level that can be used to simulate a response physics occurring in a sample, such as the MR response physics occurring in the sample using a forward model, e.g., at least Bloch equations, Liouvillian computations and/or another simulation technique, which is a function of measurement conditions. Notably, the forward model may simulate MR response physics occurring in the sample to a given external magnetic field and a RF pulse sequence that are selected from a range of measurement conditions that includes a range of possible external magnetic field values and possible RF pulse sequence. Note that the model parameters may include: a density of a type of nuclei, a longitudinal relaxation time along a direction parallel to the external magnetic field (e.g., $T_1$), a transverse relaxation time along a direction perpendicular to the external magnetic field (e.g., $T_2$) and/or an adjusted transverse relaxation time (e.g., $T_2^*$). In some embodiments, the model parameters are determined by solving (e.g., iteratively) an inverse problem without performing a Fourier transform on the additional MR measurements. For example, the iterative solving may involve repeated instances of performing an MR measurement under given measurement conditions and then updating model parameters based on a current difference between the MR measurement and an estimated or simulated MR signals or response from the forward model with the given measurement conditions. These iterations may be repeated until a convergence criterion is met, such as remaining magnitude of the difference being less than a threshold value (e.g., 1, 5 or 10%).

Next, the system may determine one or more additional medical tests (operation 618) to perform that can improve an accuracy of the first test result. Note that the determining may involve assessing benefits of a set of additional medical tests relative to costs of the set of additional medical tests and selecting the one or more additional medical tests. For example, the cost may include an opportunity cost of potential future use of the biological sample, because only a finite amount of material may be included in the biological sample that is in store. In some embodiments, the one or more additional medical tests may include: a genetic test, a metabolic test, a biochemical test, a molecular test and/or cellular analysis.

Furthermore, the system may access the biological sample (operation 620) to obtain at least a second portion of the biological sample, and may perform the one or more additional medical tests (operation 622) on at least the second portion of the biological sample to obtain one or more additional test results. For example, the accessing may involve accessing one of a set of portions of the sample having a predefined aliquoted amount needed for the one or more additional medical tests. Note that the one or more additional medical tests may be performed automatically by the system, such as without human action or human decision-making.

Additionally, the system may compute a second test result (operation 624) based at least in part on the first test result and the one or more additional test results, where the second test result has an improved accuracy relative to the first test result.

In some embodiments, the system optionally performs one or more additional operations (operation 626). For example, the system may provide a recommendation (such as a surgical procedure, a non-surgical medical treatment, a prescription for a medicine) based at least in part on the second test result when the improved accuracy is less than a threshold value.

Moreover, the system may provide the second test result, such as to an individual, to a display, to another electronic device and/or to a memory (which may store the second test result).

In some embodiments of methods 200 (FIG. 2), 400 (FIG. 4) and/or 600, there may be additional or fewer operations. Furthermore, the order of the operations may be changed, and/or two or more operations may be combined into a single operation.

While the preceding embodiments illustrated the testing technique with a forward model that uses Bloch equations, Liouvillian computations and/or another simulation technique, in other embodiments the forward model may include Maxwell's equations, a wave equation, an elasticity equation, a fluid flow equation, a thermodynamic equation, etc. to incorporate additional physical effects in a sample in response to measurement conditions that may include magnetic, electrical, vibration, acoustic, and/or another driving force.

Figure 7:
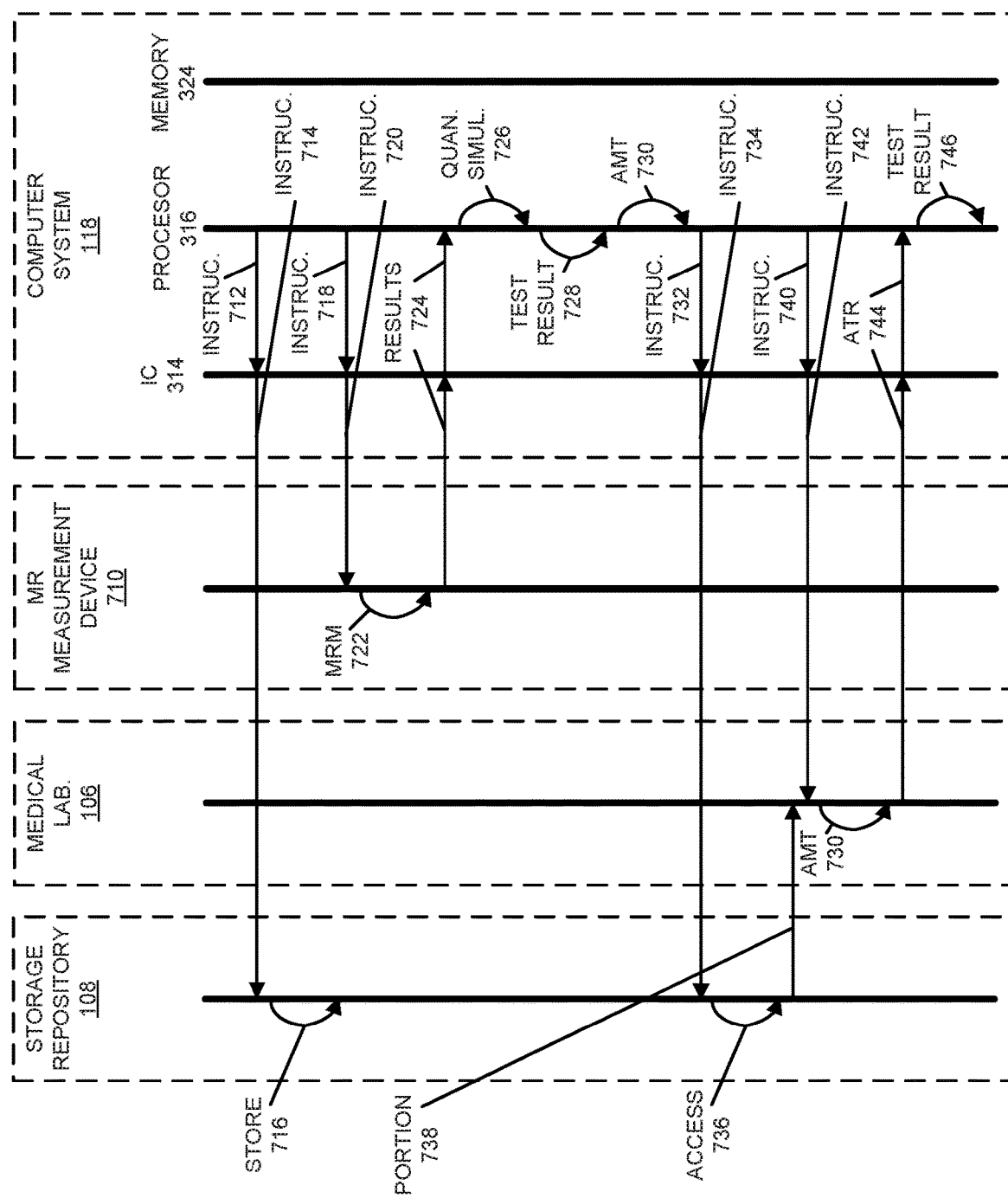
FIG. 7 is a drawing illustrating an example of communication among electronic devices in the system of FIG. 1 in accordance with an embodiment of the present disclosure.

FIG. 7 presents a drawing illustrating an example of communication among computer system 118, MR measurement device 710, medical laboratory 106, and storage repository 108. Based on instruction 712 from processor 316 in computer system 118, interface circuit 314 may provide instruction 714 to storage repository 108. After an interface circuit in storage repository 108 receives instruction 714, storage repository may store 716 a biological sample associated with a biological life form.

Then, based on instruction 718 from processor 316, interface circuit 314 may provide instruction 720 to MR measurement device 710. After an interface circuit in MR measurement device 710 receives instruction 720, MR measurement device 710 may perform one or more MR measurements (MRM) 722 on at least a portion of the biological life form. Next, the interface circuit in MR measurement device may provide results 724 of the one or more MR measurements 722 to computer system 118.

After receiving results 724, interface circuit 314 may provide results 724 to processor 316. In response, processor 316 may quantitatively simulate 726 an MR response of at least the portion of the biological life form, and may compare the one or more MR measurements 722 and the quantitative simulation to obtain test result 728.

Next, processor 316 may determine one or more additional medical tests (AMT) 730 to perform that can improve an accuracy of test result 728.

Then, based on instruction 732 from processor 316, interface circuit 314 may provide instruction 734 to storage repository 108. After the interface circuit in storage repository 108 receives instruction 734, storage repository 108 may access 736 the biological sample to obtain at least a portion 738 of the biological sample, and may provide portion 738 to medical laboratory 106. For example, portion 738 may be mailed to medical laboratory 106 and/or may be delivered by a courier. In some embodiments, medical laboratory 106 and storage repository 108 are co-located in a common facility.

Furthermore, based on instruction 740 from processor 316, interface circuit 314 may provide instruction 742 to medical laboratory 106. After an interface circuit in medical laboratory 106 receives instruction 742, medical laboratory 106 may perform the one or more additional medical tests 730 on at least portion 738 of the biological sample to obtain one or more additional test results (ATR) 744.

Next, the interface circuit in medical laboratory 106 may provide the one or more additional test results 744 to interface circuit 314 in computer system 118, which provides them to processor 316. Processor 316 may compute a test result 746 based at least in part on test result 728 and the one or more additional test results 744, where test result 746 has an improved accuracy relative to test result 728.

While FIGS. 3, 5 and 7 illustrate communication between components, electronic devices and/or computers with unilateral or bilateral communication using, respectively, single-sided or double-sided arrows, in other embodiments any given instance of communication between components, electronic devices and/or computers may involve unilateral or bilateral communication.

In the testing technique, biological samples (which are sometimes referred to as 'medical samples') are captured from a patient at an approximately periodic interval, such as weekly, monthly, every three or four months, etc. The medical samples are processed and sent to two or more storage repositories (which are sometimes referred to as 'sample storage facilities') and/or a medical laboratory or testing facility for immediate testing. The processed samples may be documented in a system and stored in the sample storage facilities until needed.

Moreover, medical information (such as new medical information) can be entered in the system at any time, which can suggest a diagnosis having a degree of uncertainty (such as a diagnosis that has an uncertainty of 50%). The system may use information about existing medical tests and/or may review advances in medical testing research (which may be entered programmatically or may be automatically generated from a scientific paper), and information about the stored medical samples to identify or determine a set of additional medical tests. Then, the system can assess benefits of the set of additional medical tests relative to costs of the set of additional medical tests to select at least one of the set of additional medical tests. The selected medical test may be recommended to reduce the uncertainty of the diagnosis (which may include eliminating one or more alternative diagnoses or diagnostic possibilities).

For example, in a study in 2013, ovarian cancer was detected by measuring a biomarker (such as serial preclinical serum CA125) and using a single threshold rule (e.g., CA125 levels above 35 U/ml) or a parametric empirical Bayes (PEB) longitudinal screening technique (e.g., CA 125 levels above 20 U/ml). Notably, a PEB longitudinal screening technique was able to detect ovarian cancer 10 months earlier and at a lower CA125 concentration than when a single threshold rule was used.

However, in a subsequent study in 2017, insulin-like growth factor-binding protein 2 (IGFBP2), lecithin-cholesterol acyltransferase (LCAT) and CA125 biomarkers worked better in combination, improving detection lead time by 5-6 months and improving identification of Type I and Type II subjects that were not identified by CA125 levels alone.

Given this new medical knowledge, the system may review a list of available tests and available documented and stored medical samples, and may determine that IGFBP2 and LCAT are included as available medical tests. Moreover, the system may have already tested for CA125 (which was the state of the art in 2013). The additional medical tests may be ranked by a combination of reduction in the uncertainty of the diagnosis, and the costs of the medical tests. In this example the system may determine that costs of the medical tests for the two additional biomarkers (IGFBP2 and LCAT) may be, respectively, $25.00 and $47.00, and that these are the lowest costs for the medical tests in the set of additional medical tests. Furthermore, the system may determine that test results for the two additional biomarkers (IGFBP2 and LCAT) will provide earlier and more accurate diagnosis using the previously tested medical sample. In order to remain within a budget, the system may query an insurance company policy for information about covered medical testing expenses and/or may obtain patient or medical professional approval of the expense. Alternatively, the system may execute a standing order (from an insurance company, a patient or a medical professional) to perform any medical tests with costs under a fixed amount (e.g., $100) or within a total combined testing cost limit (e.g., $500). Thus, the system may execute standing instructions to order medical tests below a cost threshold or a physician or medical professional can authorize (e.g., via a single mouse click, voice instruction, a key press, a message send, etc.) ordering of a medical test recommended by the system.

In response, the system may re-order medical tests on historical (and stored) medical samples for at-risk patients who tested at CA125 levels above 35 U/ml or above. Using the biomarker levels from one or more additional medical tests performed on the historical medical samples (which may be accessed in a storage repository), the uncertainty of the diagnosis may be reduced, which can relieve a patient who may be concerned about a possible cancer diagnosis. Alternatively, the improved diagnostic accuracy may provide earlier and more accurate detection to a patient that has cancer, which will give the patient more treatment options.

When a condition is tentatively discovered at a given time after the new research results are published (such as based on a CA125 level above 35 U/ml in the preceding example), additional medical tests (e.g., IGFBP2 and LCAT biomarkers) can be ordered from one of the previously acquired and stored medical samples in order to determine additional information that improves the diagnosis, without having to draw or acquire a new medical sample from a patient.

Note that the biomarker medical test(s) can be abstracted to any suitable biomarker medical test(s) where one or more biomarker values have surpassed a single threshold value or have a rate of change as a function of time that could cause a projection or extrapolation of a biomarker to surpass a single threshold value. In some embodiments, a biomarker may be screened using a PEB longitudinal screening technique or another analysis technique.

Moreover, an additional medical test may be selected based on the medical samples available, the types of medical tests available at a previous time, and/or the types of tests currently available that were not previously available.

While the preceding example used ovarian cancer as an illustrative example, the testing technique may be used with a wide variety of biomarkers and medical tests, as well a variety of potential medical conditions or diagnoses, such as prostate cancer, a chronic disease, an episodic disease, an infectious disease, aging, etc.

Figure 8:
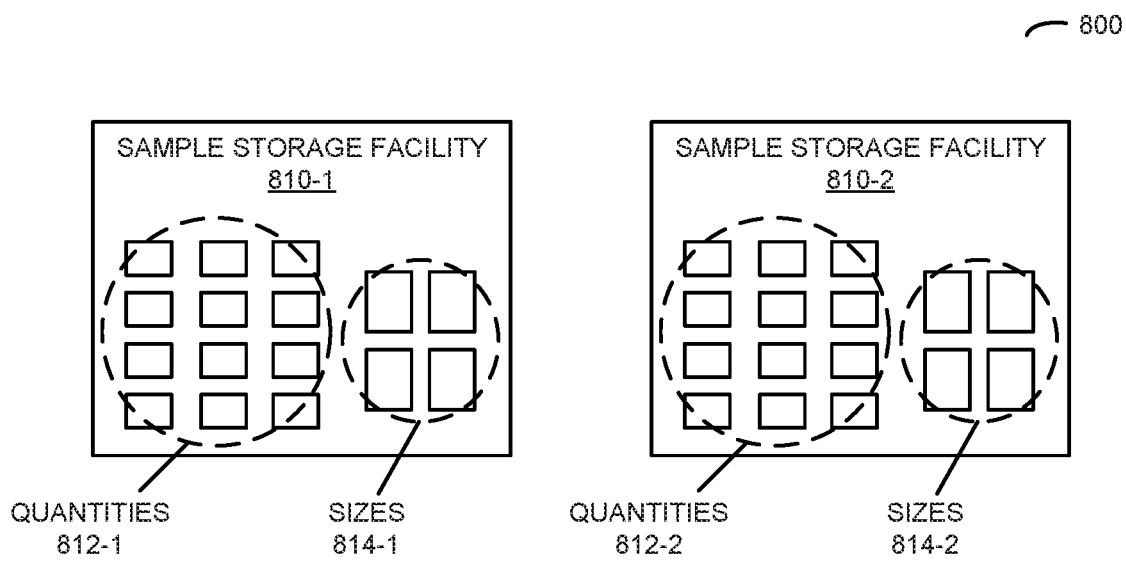
FIG. 8 is a drawing illustrating an example of a storage repository system for storing biological samples in accordance with an embodiment of the present disclosure.

FIG. 8 presents a drawing illustrating an example of a storage repository system 800 for storing biological samples. Medical samples may be captured from an individual or a patient at an approximately periodic interval over time (e.g. hourly, daily, weekly, monthly, quarterly, semiannually, annually, biannually, etc.). The medical samples may be processed and sent to at least two sample storage facilities 810 (such as sample storage repositories) for diversity in storage, which provides fault tolerance. Notably, if the medical samples were stored at a single sample storage facility, and the sample storage facility lost power, the medical samples (and, thus, the entire medical sample history) would be destroyed and valuable medical history information would be lost. Consequently, sample storage facilities may be located in seismically stable locations with backup power generation and disaster-recovery power planning. Note that a sample storage facility may also have the ability to ship medical samples offsite quickly and securely in the case of a major disaster.

For additional diversity and redundancy, medical samples may also be stored at different cryostorage temperatures (such as −80 C and at −140 to −180 C in a vapor phase above liquid nitrogen) to prevent degradation of the medical samples. The vapor phase temperatures above liquid nitrogen may be selected for long-term storage or for the study of metabolites. Notably, this range of temperatures may cool water below its glass transition temperature and may significantly reduce the migration of oxygen and other radicals within medical samples. However, the higher temperatures of −80 C may be acceptable for some types of medical tests, including testing of DNA and proteins, which can result in a more cost-effective and/or efficient sample storage facility.

Note that medical sample processing may involve one or more operations to either preserve a medical sample in its original state, or to pre-process the medical sample in preparation for future medical tests that may be performed. For example, processing of a medical sample can include dividing the medical sample into smaller quantities 812 (aliquoting) to enable it to be used in future medical tests and/or using different medical sample values or sizes 814.

Moreover, for fluid samples, aliquots may be created for different medical testing technologies that are known or likely to be useful in future laboratory testing. By saving an amount of fluid that is close to what is needed by the medical laboratory, as much of the medical sample as possible may be held in reserve for running additional medical tests on another occasion. Note that aliquoting may also reduce freeze and thaw cycles, as ideally a medical sample may only ever be frozen once and thawed once.

In the preceding example, a blood test from a patient may use 7.5 ml of blood. Consequently, a medical sample may be captured or acquired in a 7.5 ml tube. The tube can be centrifuged, and then 5×500 µl volumes can be aliquoted from the medical sample tube and stored in a 0.5 ml cryotube. Note that volumes of 10 µl, 25 µl, 50 µl, 100 µl, 150 µl, 200 µl, 300 µl, 400 µl and/or 500 µl can also be used, and biomarker medical tests can be destructively performed on one or more of the aliquoted and stored amounts.

Furthermore, for serum, a medical sample may be prepared in a serum separator tube, spun in a centrifuge after clotting, and then aliquoted. Note that many existing laboratory tests use this medium for testing. In addition, antibody studies can be performed on this material. Basically, by separating the clotting material from the blood, the remaining medical sample is somewhat cleaned of bulk proteins and other clotting factors, so lower-abundance proteins can be easier to analyze.

Additionally, for plasma, a medical sample may be prepared in K2-EDTA (an anti-coagulant) with two centrifuge spins (e.g., a slow first spin for 10 min. at 208 relative centrifugal force or RCF), and then a faster spin for 10 min. at 1582 RCF to reduce cell lysing. By separating plasma from whole cells, a truer signal of what is in the blood (i.e., outside of cells) may be obtained relative to the case of serum, where some constituents are taken out of solution by the clotting process. New medical tests for metabolomics (including lipidomics, and proteomics) may be performed on this medical sample to get a better representation of blood contents in sensitive assays. The prepared medical sample may be stored in liquid nitrogen (−196 C) because of its value in upcoming of future assays.

For plasma with cfDNA preparation, a medical sample may be processed as above, but with an additional centrifuge spin for 10 min. at 1777 RCF after the plasma has been pipetted off the cell layers. With a cell lysing preventative solution and this extra cleaning centrifugation, a very clean signal of the DNA fragments present in the extracellular fluid in the blood stream may be provided. This may provide improved understanding about cells that are releasing this genetic material as they die or create signals for other parts of the body. Consequently, the medical sample can provide a picture of somatic DNA mutation.

Moreover, for whole blood DNA in-vitro diagnostic preparation, processing may include preventing clotting of a whole blood sample using K2-EDTA. Then, DNA in the medical sample may be preserved using reagents added by a tube manufacturer. This may be appropriate to DNA testing, but could potentially be used to test properties of the immune system or the contents of the red blood cells (although these cells would be mostly lysed after a freeze cycle).

Furthermore, for saliva, the processing of a medical sample may include freezing at least some of the saliva directly, and may provide another DNA source for germline genome analysis, microbiome analysis and/or hormone analysis, because saliva can concentrate signaling molecules in the body.

Additionally, for urine, a medical sample can be used to retest incumbent urinalysis or to test for other metabolic disorders not covered in standard testing.

In some embodiments, an instance of a medical sample at a given time may include a separator tub with 7.5 ml of serum, four separator tubes with 8.5 ml each of serum, two tubes each with K2-EDTA plasma, a tube with 10 ml of K2-EDTA plasma, a tube with 10 ml of K2-EDTA plus cell/DNA preservative plasma and/or a tube with 2.5 ml of whole blood with DNA in-vitro diagnostic preparation. The tube with 10 ml of K2-EDTA plus cell/DNA preservative plasma may be processed in a centrifuge at 208 RCF for 10 min. and 1582 RCF for 10 min. Then, after the centrifuge plasma is taken off the top, the remainder may be processed in a centrifuge at 1777 RCF for 10 min. and the plasma may be pipetted into four cryotubes. Moreover, tubes with K2-EDTA plasma may be processed in a centrifuge at 208 RCF for 10 min. and 1582 RCF for 10 min. Then, the plasma may be pipetted into 15 cryotubes. Furthermore, after a clotting time, the tubes of serum may be processed in a centrifuge at 1777 RCF for 10 min., and then the serum may be pipetted into five cryotubes.

Note that a broad metabolomics test may use 50 µl of EDTA plasma from a 200 µl cryotube. Moreover, a proteomics test may use 50 µl of EDTA plasma from a 200 µl cryotube and 200 µl of EDTA plasma from a 200 µl cryotube. Furthermore, a genomics test may use 2.5 ml of whole blood with DNA in-vitro diagnostic preparation from a cryotube. Additionally, a lipidomics test may use 0.5 ml of EDTA plasma from a cryotube. In some embodiments, a cell-free DNA analysis test may use 1 ml of cfDNA plasma from a a cryotube.

We now describe determination of one or more model parameters in a forward model. This forward model may be a 3D model of voxels in at least a portion of a biological life form, and may include model parameters in the Bloch equations for each of the voxels. Notably, with a quasi-static magnetic field $B_0$ along the z axis, the Bloch equations are $$\frac{dM_x(t)}{dt} = \gamma \cdot \left(\vec{M}(t) \otimes \vec{B}(t)\right)_x - \frac{M_x(t)}{T_2},$$

$$\frac{dM_y(t)}{dt} = \gamma \cdot \left(\vec{M}(t) \otimes \vec{B}(t)\right)_y - \frac{M_y(t)}{T_2}, \text{ and}$$

$$\frac{dM_z(t)}{dt} = \gamma \cdot \left(\vec{M}(t) \otimes \vec{B}(t)\right)_z - \frac{M_z(t) - M_0}{T_1},$$

where $\gamma$ is the gyromagnetic ratio, $\otimes$ denotes a vector cross product and $\vec{B}(t) = (B_x(t), B_y(t), B_0 + \Delta B_z(t))$ is the magnetic field experienced by a type of nuclei in the portion of the biological life form. The model parameters in the Bloch equations may include $T_1$, $T_2$, a density of a type of nuclei, diffusion, velocity/flow, temperature, and/or magnetic susceptibility. Note that there may be different model parameters for different types of nuclei for each of the voxels. Moreover, note that the Bloch equations are a semi-classical, macroscopic approximation to the dynamic response of the magnetic moments of the type of nuclei in the portion of the biological life form to a time-varying magnetic field. For example, there may be 67 M cells in a 1 mm$^3$ voxel.

In principle, the solution space for the model parameters in the Bloch equations for the portion of the biological life form may be underdetermined, i.e., there may be significantly more model parameters to be determined than there are observations with which to specify or constrain the model parameters. Therefore, the testing technique may leverage additional information to constrain or reduce the dimensionality of the problem. For example, an aspect of the anatomy of the portion of the biological life form may be determined using other imaging techniques, such as computed tomography, x-ray, ultrasound, etc. Moreover, regions that do not look like (i.e., that have very different MR signals) than a targeted type of tissue (such as heart tissue) may be excluded from the forward model. In this way, for example, regions that consist of air may be excluded. Alternatively or additionally, tissue that deviates significantly from the expected MR signals or response based on previous MR measurements (e.g., anomalies or changes) may become the focus of the forward model, such as by using a contour map (e.g., a cubic spline) to bound the regions (or specify a boundary of the regions) where there are significant differences. In some embodiments, the error between MR measurements and simulated or estimated MR signals or response may be represented using one or more level-set functions, and the boundaries of regions with errors exceeding a threshold value may be determined based on the intersection of a plane corresponding to the threshold value and the one or more level-set functions. In addition, by performing the additional MR measurements (such as scans) at different magnetic-field strengths $B_0$ (which may provide similar information to pseudorandom pulse sequences) using different pulse sequences and/or different MR techniques, the ratio of model parameters to observations may be reduced, thereby simplifying the determination of the forward model.

For example, if a portion of the biological life form included one voxel, there may be 4-10 MR model parameters (which specify an invariant MR signature or a forward model) that need to be determined for a particular type of tissue. If the voxel includes M types of tissue, there may be 4M-10M forward model parameters (which may specify M invariant MR signatures) that need to be determined for the particular type of tissue. As the number of voxels increases, this can appear to be a daunting problem.

However, because different types of nuclei have different Larmor frequencies, the spatial distribution of the types of nuclei and their local concentrations may be determined from the additional MR measurements. Then, a predefined anatomical template for the biological life form (or a portion of the biological life form), with associated initial model parameters for a forward model, may be scaled to match the spatial distribution of the types of nuclei and their local concentrations.

Next, for a type of tissue (such as a particular organ), the forward model parameters may be iteratively refined as the size of the voxels is progressively decreased (and, thus, the number of voxels is increased). This analysis may be driven by the error between the MR measurements and simulated or estimated MR signals or response using the forward model. Over time, the focus during the training will be on the residual regions with errors that are larger than a convergence criterion. For example, the model parameters in the forward model may be trained based on MR measurements at one magnetic-field strength and then the error may be determined based on the predictions of the forward model at another magnetic-field strength. Furthermore, note that initially the forward model may assume that there is no contribution or interaction between different voxels. However, as the error and the voxel size are reduced, subsequently such contributions and/or interactions may be included when training the forward model.

In order to facilitate this fitting or computational approach, the testing technique may determine 'surface signatures,' as opposed to 1D signatures. For example, using measurements at multiple magnetic-field strengths or in the presence of known magnetic-field disturbances (such as rotation), a set of MR trajectories in a multidimensional space may be determined and may be used to determine the invariant MR signature(s) and/or forward models. Note that each MR trajectory may be defined by a magnetic-field function rather than a fixed magnetic-field strength.

In an exemplary embodiment, a simulation that is used to determine the forward model may be vertex/voxel centric. Using a physical model (such as a Bloch-equation-based model) running at each vertex, the system may 'apply' RF pulse sequences or disturbance to the physical model of the portion of the biological life form being measured or scanned. For example, a message may be broadcast to the vertices that describe the disturbance in terms of the physics. Each of the vertices may compute its predicted change in state and the resulting forces and energies, which are then relayed as messages to adjacent vertices about the forces and energies exported from that vertex. When all the vertices have generated a message, the message has been forwarded to the adjacent vertices and the state of the system has been updated, a time interval in the calculation may be complete. This approach can be generalized so that the message is forwarded to non-cyclical paths of length N (where N is an integer) radiating out from the vertex to improve the accuracy of the simulation.

Once the state has been updated, a computational technique can be run over the new computed state and then compared to the measured state. The error may be the difference between the predicted state and the measured state. As the computational technique is applied, the system may determine how to improve or optimally assign the current state to each vertex in a way that reduces or minimizes the global error. Next, the system may choose a new set of perturbations for the system and may broadcast these as a new message to the vertices, as well as executing this disturbance physically on the biological life form being scanned or measured. In this way, the system may provide real-time or near-real-time analysis and feedback during the testing technique. Therefore, in some embodiments, the determination of the model parameters may occur currently with the MR measurements. Indeed, in some embodiments the model parameters may be determined continuously during the MR measurements.

Thus, the inverse problem of determining the MR model parameters based on MR measurements may be 'solved' by reducing or minimizing the error or difference between the MR measurements and simulated or estimated MR signals or response that are generated based on the forward model, characteristics of the MR scanner (such as magnetic-field inhomogeneity) or the MR measurement device (which may be different from an MR scanner) and the scanning or measurement instructions used to acquire the MR measurements. In some embodiments, the inverse problem is solved using one or more computational techniques, including: a least-squares technique, a convex quadratic minimization technique, a steepest descents technique, a quasi-Newton technique, a simplex technique, a Levenberg-Marquardt technique, simulated annealing, a genetic technique, a graph-based technique, another optimization technique and/or Kalman filtering (or linear quadratic estimation).

Note that the inverse problem may be solved using dynamic programming. Notably, the problem may be divided up and performed by multiple computers in parallel, e.g., in a cloud-based computing system. For example, a particular thread may attempt to solve the inverse problem for particular scanning or measurement instructions. Multiple potential model parameter solutions generated by the computers (or processors) may be combined (e.g., using linear superposition) to determine an error metric that is reduced or minimized using the one or more computational techniques.

Moreover, as described previously, the inverse problem may be solved iteratively by first attempting to find suitable model parameters (e.g., model parameters that reduce or minimize the error between the MR measurements and simulated or estimated MR signals or response) for the forward model using a coarse voxel size and then progressively finding suitable model parameters with smaller voxel sizes. Note that the final voxel size used in this iterative procedure may be determined based on the gyromagnetic ratio of a type of nuclei being scanned or measured. The voxel size can also be determined based on the kind of 'query' that is made to the biovault or that forms the based on the MR measurement plan, the current hardware configuration and/or hardware limitations. Furthermore, the voxel size or locations may also be chosen so that a voxel is evenly portioned into a set of subvoxels, or so that there is certain amount of overlap with preview voxel sizes to effectively 'oversimple' the overlapping region and potentially further localize where an MR signal originates. This last technique may be akin to shifting the entire gradient system in one or more dimensions by a distance dx that is less than a characteristic length of the voxels (such as a length, a width or a height of the voxels). In some embodiments, the voxel size in the forward model is smaller than that used in the MR measurements (i.e., the forward model may use a super-resolution technique).

Additionally, the forward model may include simulations of dynamics, such as motion associated with: respiration, a heartbeat, blood flow, mechanical motion, etc. (Thus, there may be additional terms in the Bloch equations for diffusion, thermometry, spectroscopy, elastography, etc. Consequently, the forward model may be based on the Bloch-Torrey equations, etc.) For example, when a voxel contains a space that has a fluid flowing through it (such as in a vein), the flow of the liquid may be simulated by building a map of the flow directions and velocity magnitudes in the biological life form being scanned or measured to be accounted for in the computation of the invariant MR signature or the forward model. Furthermore, when scanning a human or an animal, the forward model may include the resting motion (such as that associated with respiration, a heartbeat, etc.). In some embodiments, in order to facilitate calculation of the forward model, measured MR signals and/or other temporal measurements may be synchronized with or relative to a reference clock or a biological time period.

The forward model may be used to predict how the biological life form will respond to particular scanning or measurement instructions. Notably, the forward model may be used to simulate or estimate the MR signals or response for a particular MR scanner or a particular MR measurement device having particular characteristics, for particular scanning or measurement instructions and/or for a particular biological life form (such as an individual who has a medical history, previous MR scan or measurement results, etc.). Stated different, an invariant MR signature or a forward model may be used to determine representations or projections (i.e., the MR signals) in particular contexts, such as based on the particular characteristics of the MR scanner or MR measurement device, the particular scanning or measurement instructions and/or the particular biological life form.

Thus, the forward model may allow system 100 (FIG. 1) to perform active learning. Notably, the forward model may be iteratively fit or determined based on 'queries' generated by a learning system or a learning engine (which may be implemented in computer system 118 in FIG. 1). Moreover, the queries generated by the learning engine may include different magnetic-field strengths $B_0$, different RF pulse sequences and/or different ultrasonic pulse sequences that are based on confidence intervals for model parameters in the forward model. Consequently, the learning engine may use the MR measurements in response to these queries to determine unknown model parameters in the forward model and/or model parameters having a poor accuracy (such as a confidence interval greater than 0.1 1, 5 or 10%). More generally, the adaptive learning performed by system 100 (FIG. 1) may be based on a wide variety of measurements, such as optical/infrared spectroscopy, x-ray, computed tomography, proton beam, photoacoustic, ultrasound, etc.

In an exemplary embodiment, computer system 118 (FIG. 1) first approximates the model parameters in the forward model and computes the error (or difference vector) between the MR measurements and simulated or estimated MR signals or response based on this initial forward model. Note that when there are multiple candidate model parameter solutions (having similar errors) to the inverse problem for a thread corresponding to particular scanning or measurement instructions, computer system 118 (FIG. 1) may keep the candidates (i.e., a unique model parameter solution may not be identified at this point in the calculation). Alternatively, if there is no unique model parameter solution within a desired error range (such as less than 50, 25, 10, 5 or 1%), the best (least-error) model parameter solution may be kept. In addition, when there is no model parameter solution within the desired error range, computer system 118 (FIG. 1) may modify the scanning or measurement instructions.

Moreover, computer system 118 (FIG. 1) may compute first and second derivatives along a surface(s) of model parameter solutions in the biological life form. (In order to facilitate calculation of a derivative, note that the model parameters may be represented using one or more level-set functions.) A set of voxels along the line where the first derivative is zero may be identified. This set of voxels may be fit using a cubic spline with a reduced or minimum error between the voxel positions and the cubic spline. This fitting operation may be repeated at all the boundaries in the model-parameter-solution space. Moreover, the largest continuous surface within the boundary defined by the cubic splines may be determined and the model-parameter-solution calculation may be repeated to determine a new continuous surface that is within the previous continuous surface. This generalized framework may reduce or minimize the error across intra-voxel volumes, thereby improving the agreement between the MR measurements and the simulated or estimated MR signals or response based on the forward model.

For example, the inverse problem may be solved using a Jacobian matrix of the model parameters for the voxels in the forward model and Newton's method to iteratively modify the model parameters for the voxels based on how perturbations in the model parameters affect the difference between the MR measurement and the estimated MR signal or response. During the RF pulses, the MR signal or response may be estimated by solving a system of equations (such as the Bloch equations) numerically because, for $^1$H, the RF pulses are close to or at Larmor frequency for $^1$H (this may not be the case for other types of nuclei). Notably, Runge-Kutta method 4 may be used to determine the numerical solution to a differential equation for the rotating coordinate system. The effect of gradient changes can be solved analytically because the time scale (milliseconds) is much lower than the Larmor frequency.

In some embodiments, the dynamics of the magnetization associated with the nuclei spins is decomposed into relaxation along the direction of the external magnetic field per $T_1$ and rotation and relaxation per $T_2$ in plane perpendicular to the direction of the external magnetic field. However, the analysis in the testing technique does not require an assumption about a rotating frame of reference or a particular direction of polarization. Note that the magnitude and/or the direction of the external magnetic field may be changed as a function of time. This may allow the external magnetic field to be swept over a range of magnitudes and/or directions in order to characterize anisotropy (as opposed to the structured excitation using in existing MR techniques), such that the relaxation times that are determined are with respect to or associated with different axes or directions. Alternatively or additionally, the testing technique may use weaker external magnetic fields and/or external magnetic fields that have more spatial inhomogeneity than existing MR techniques. Indeed, the polarizing external magnetic field may be weaker than the excitation field, such as the RF pulses.

In some embodiments, the analysis in the testing technique alternates between the Bloch equations (or something more sophisticated, such as the full Hamiltonian) and Maxwell equations in the forward model to rapidly calculate magnetic properties of the sample volume and electric properties of the sample volume. In this way, the estimates provided using one forward model can be used to regularize the estimates from the other forward model. This approach may accelerate converge and may allow the permittivity and the conductivity of each voxel to be determined in the model parameters for the forward model.

In an exemplary embodiment, 2-3 iterations of MR measurements and modification of the model parameters in the forward model are needed to obtain values of the model parameters for the voxels to less than 1% accuracy. This may be an order of magnitude better than MR fingerprinting and, at least in some embodiments, may be determined without requiring the use of pre-existing data structure with prior results for the model parameters.

However, in some embodiments, a priori knowledge is used to constrain the inverse problem. For example, predetermined or predefined ranges for the model parameters in different types of tissue may be used to determine the initial values of the model parameters. Alternatively or additionally, values of the model parameters based on previous MR measurements may be used as the initial values of the model parameters in a current instance of the analysis in the testing technique. Other constraints during the analysis may include: thermodynamic constraints on heat flow (from hot to cold) for perfusion or MR thermometry to quantify metabolism and/or Maxwell's equations constraints.

Note that the testing technique may allow spatial distributions of relaxation times and densities in inhomogeneous tissues to be determined. For example, the testing technique may allow voxel-by-voxel densities and relaxation times for an inhomogeneous sample to be estimated.

In some embodiments, the geometry of the voxels in the forward model may be calculated to the accuracy of the estimated MR signals or response or to reduce the error between the MR measurements and the estimated MR signals or response. For example, the voxels may be represented as a graph, which may facilitate auto-segmentation and/or registration. The spatial resolution in the forward model may be higher than is typically used for or associated with the strength of the external magnetic field (i.e., super resolution). In an exemplary embodiment, there are 512×512 voxels or 1024×1024 voxels at a magnetic-field strength of 3T. Note that the voxel size may be less than $0.25^3$ mm$^3$.

In order to speed up the determination of the model parameters in the testing technique, compressed sensing may be used. For example, regions with air may be dropped. Moreover, because there may be more equations than unknowns, a down-selection technique may be used during the analysis. For example, linearly independent rows in a system of equations may be selected. Alternatively or additionally, the down selection may be: random, a subset of the equations that are most orthogonal, a subset of the equations that linearly independent in a particular setting, a subset of the equations that maximize the volume (such as a submatrix with the largest determinant), etc.

As noted previously, the external magnetic field and/or the RF sequence may be modified or changed during the MR measurements. In some embodiments, the 'excitation' may be chosen to reduce or minimize the error in the next iteration of the analysis. For example, the external magnetic field and/or the RF sequence may be changed based on how well conditioned the Jacobian is.

Note that the inputs to and the outputs from the analysis in the testing technique may be stored for future use. Note that the inputs may include information about the measurement device and how the measurements were performed. This may allow accuracy to be traded off with acquisition time. In addition, it may allow the analysis to be continued offline over long times.

Moreover, the model parameters in the forward model may be determined sequentially based on the time scales associated with physical phenomena. Notably, temporal decomposition may allow the density to be determined, followed by $T_1$, $T_2$, model parameters for flow, model parameters for diffusion, model parameters for thermometry, etc. This approach may be more efficient, because physical phenomena on longer time scales may require longer RF sequences.

As noted previously, the testing technique may not require the use of a Fourier transform or synchronous averaging. Instead, the model parameters may be determined rapidly as long as the initial values of the model parameters are reasonable (such as within 25, 50, 100, 500 or 1000% of the correct model parameter values). Alternatively or additionally, a longer RF sequence may be used.

Furthermore, the variation in the model parameters in different types of tissue may allow the types of tissue to be segmented. Notably, at a spatial boundary of two types of tissue there may be a discontinuity in a dimension in a high-dimensional space of the model parameters, such as at a boundary between adjacent voxels. For example, this segmentation technique may be used to distinguish between cerebrospinal fluid and the meninges. Furthermore, the variation in the model parameters for different types of tissue may be used to constrain the search space when solving the inverse problem.

As an illustration, there may be considerable variation of $T_1$ and $T_2$ in different types of tissue. For example, cerebrospinal fluid may have a $T_1$ between 0.8-20 s and a $T_2$ of 110-2000 ms. white matter may have a $T_1$ between 0.76-1.08 s and a $T_2$ of 61-100 ms. gray matter may have a $T_1$ between 1.09-2.15 s and a $T_2$ of 61-109 ms. meninges may have a $T_1$ between 0.5-22 s and a $T_2$ of 50-165 ms. muscle may have a $T_1$ between 0.95-1.82 s and a $T_2$ of 20-67 ms, and adipose may have a $T_1$ between 0.2-0.75 s and a $T_2$ of 53-94 ms.

In some embodiments, the medical sample is a solution and the number of voxels is variable. Given an external magnetic field strength, and a medical sample from a biological life form that been previously tested (e.g., because it was the same medical sample or another medical sample was drawn from the biological life form at the same time), then some a priori information is available about the medical sample. Consequently, if there is a hypothesis about the existence of a specific molecule or protein and something is known about the distribution of other molecules or proteins in the medical sample based on previous measurements, then an MR signal or response can be simulated when a particular RF sequence applied to the medical sample. This may help quantify the specific molecule or protein. Moreover, the RF sequence may be applied to the sample and the MR measurement may be performed and compared to the estimated or simulated MR signal or response to determine the amount of agreement. Next, an inverse problem can be solved for a specific distribution of model parameters (e.g., chemicals or nuclei) regardless of whether there is one or multiple voxels.

We now describe embodiments of an electronic device. FIG. 9 presents a block diagram illustrating an example of an electronic device 900, such as one of electronic devices 110 or computer system 118 in FIG. 1. This electronic device includes processing subsystem 910 (such as an integrated circuit or control logic), memory subsystem 912, and networking subsystem 914. Processing subsystem 910 includes one or more devices configured to perform computational operations and/or to process search queries received via networking subsystem 914. For example, processing subsystem 910 can include one or more microprocessors, graphical processing units (GPUs), application-specific integrated circuits (ASICs), microcontrollers, programmable-logic devices, and/or one or more digital signal processors (DSPs).

Memory subsystem 912 includes one or more devices for storing data and/or instructions for processing subsystem 910 and networking subsystem 914. For example, memory subsystem 912 can include dynamic random access memory (DRAM), static random access memory (SRAM), and/or other types of memory. In some embodiments, instructions for processing subsystem 910 in memory subsystem 912 include: one or more program modules or sets of instructions (such as program instructions 922 or operating system 924), which may be executed by processing subsystem 910. Note that the one or more computer programs may constitute a computer-program mechanism. Moreover, instructions in the various modules in memory subsystem 912 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 910.

In addition, memory subsystem 912 can include mechanisms for controlling access to the memory. In some embodiments, memory subsystem 912 includes a memory hierarchy that comprises one or more caches coupled to a memory in electronic device 900. In some of these embodiments, one or more of the caches is located in processing subsystem 910.

In some embodiments, memory subsystem 912 is coupled to one or more high-capacity mass-storage devices (not shown). For example, memory subsystem 912 can be coupled to a magnetic or optical drive, a solid-state drive, or another type of mass-storage device. In these embodiments, memory subsystem 912 can be used by electronic device 900 as fast-access storage for often-used data, while the mass-storage device is used to store less frequently used data.

Figure 9:
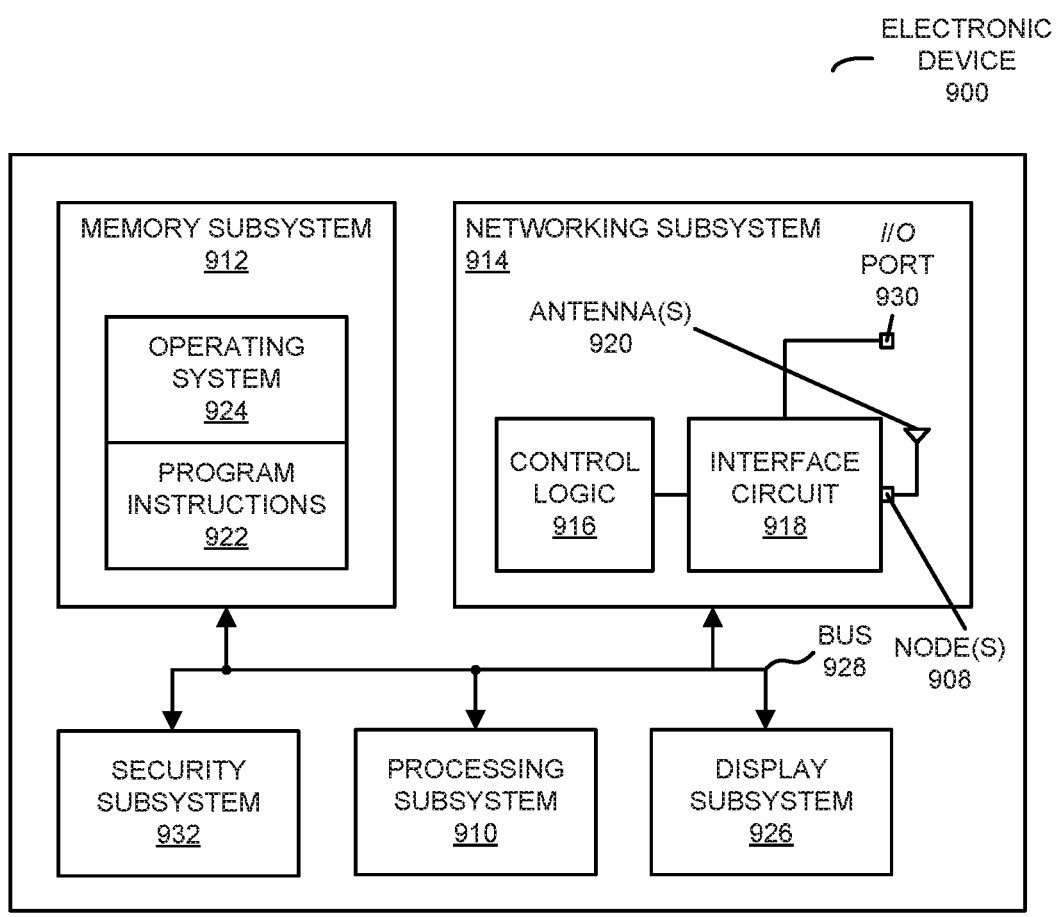
FIG. 9 is a block diagram illustrating an example of an electronic device in the system of FIG. 1 in accordance with an embodiment of the present disclosure.

While FIG. 9 illustrates electronic device 900 as including memory subsystem 912, in some embodiments memory subsystem 912 includes remotely accessible memory, such as: a cloud-based storage system, a high-capacity network attached mass-storage device (e.g., network attached storage), an external hard drive, a magnetic-tape backup system, a cluster of servers, a cloud-based storage provider, a cloud-computing provider, a medical records archive service, or any other suitable archive devices. Note that processing subsystem 910 may interact with remotely accessible memory via an API and networking subsystem 914 to store and/or request information.

In some embodiments, blocks of data are stored in memory subsystem 912 using a blockchain or similar cryptographic hash technology to detect unauthorized modification or corruption of records. Moreover, the data can be anonymized so that the identity associated with a subject is anonymous unless the subject gives permission or authorization for this information to be released.

Figure 10:
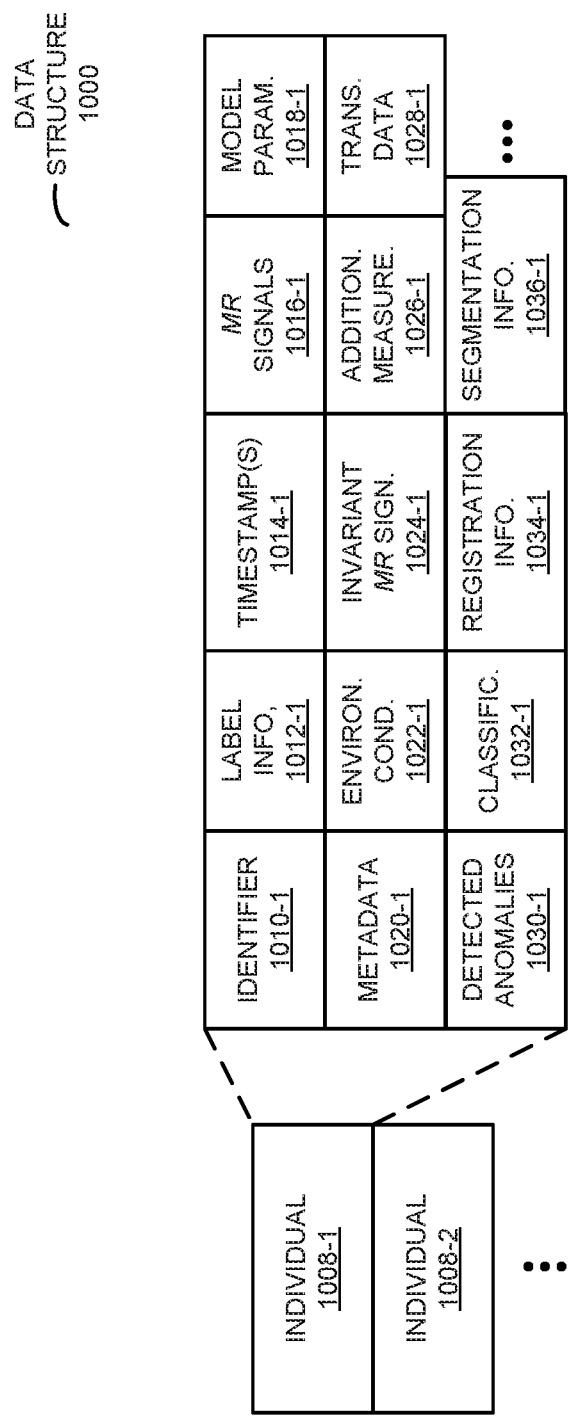
FIG. 10 is a drawing illustrating a data structure for use in conjunction with the electronic device of FIG. 9 in accordance with an embodiment of the present disclosure.

Moreover, memory subsystem 912 may store or may have access to medical records for one or more patients that are associated with one or more healthcare providers. FIG. 10 presents a drawing illustrating an example of a data structure 1000 for use in electronic device 900 (FIG. 9). Notably, data structure 1000 may include: an identifier 1010-1 of an individual 1008-1, label information 1012 (such as age, gender, biopsy results and diagnosis if one has already been made and/or any other suitable biological sample information, such as type of biological sample, which can include blood, saliva, hair, sweat, urine, tears, mucus, stomach acid, stool, cerebral spinal fluid, tissue samples, etc.), timestamps 1014 when data was acquired, received MR signals 1016 (and, more generally, raw data), MR capture and model parameters 1018 (including the voxel size, speed, resonant frequency, T1 and T2 relaxation times, signal processing techniques, RF pulse techniques, magnetic gradient strengths, the variable magnetic field $B_0$, the pulse sequence, etc.), metadata 1020 (such as information characterizing individual 1008-1, demographic information, family history, optional segmentation data, data generated from or in response to the raw data, etc.), environmental conditions 1022 (such as the temperature, humidity and/or barometric pressure in the room or the chamber in which individual 1008-1 was measured), a determined invariant MR signature 1024, one or more additional measurements 1026 of physical properties of individual 1008-1 (such as weight, dimensions, images, etc.), transformed data 1028 generated from or in response to MR signals 1016 (such as an estimated invariant MR signature), optional detected anomalies 1030 (which, for a particular voxel, may include information specifying one or more of detected anomalies 1030), optional classifications 1032 of detected anomalies 1030), registration information 1034 and/or segmentation information 1036. Note that data structure 1000 may include multiple entries for test results over time, including: genetic testing, cell-free DNA/RNA, epigenetic testing, transcriotomic testing, proteomic testing, lipidomic testing, metabolomic testing, microbiomic testing, etc. In some embodiments, data in data structure 1000 is encrypted using a blockchain or a similar cryptographic hash technique to detect unauthorized modification or corruption of records. Moreover, the data can be anonymized prior to storage so that the identity of an individual is anonymous unless the individual gives permission or authorization to access or release the individual's identity.

More generally, data structure 1000 may include medical records for different patients or individuals 1008. These medical records may include: timestamps 1014 when the measurements were performed, measurement data, measurement configurations, analysis or tests results and optional patient metadata. Note that the inclusion of separate measurement data and measurement configurations may facilitate retrospective analysis of the medical records at subsequent time stamps 1014 based on new or additional information (such as additional test results) to determine new or revised analysis results.

Referring back to FIG. 9, networking subsystem 914 may include one or more devices configured to couple to and communicate on a wired, optical and/or wireless network (i.e., to perform network operations), including: control logic 916, an interface circuit 918, one or more antennas 920 and/or input/output (I/O) port 930. (While FIG. 9 includes one or more antennas 920, in some embodiments electronic device 900 includes one or more nodes 908, e.g., a pad, which can be coupled to one or more antennas 920. Thus, electronic device 900 may or may not include one or more antennas 920.) For example, networking subsystem 914 can include a Bluetooth networking system (such as Bluetooth Low Energy), a cellular networking system (e.g., a 3G/4G network such as UMTS, LTE, etc.), a universal serial bus (USB) networking system, a networking system based on the standards described in IEEE 802.11 (e.g., a Wi-Fi networking system), an Ethernet networking system, and/or another networking system.

Networking subsystem 914 includes processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for the network system. Moreover, in some embodiments a 'network' between the electronic devices does not yet exist. Therefore, electronic device 900 may use the mechanisms in networking subsystem 914 for performing simple wireless communication between the electronic devices, e.g., transmitting advertising or beacon frames and/or scanning for advertising frames transmitted by other electronic devices as described previously.

Within electronic device 900, processing subsystem 910, memory subsystem 912, and networking subsystem 914 are coupled together using bus 928. Bus 928 may include an electrical, optical, and/or electro-optical connection that the subsystems can use to communicate commands and data among one another. Although only one bus 928 is shown for clarity, different embodiments can include a different number or configuration of electrical, optical, and/or electro-optical connections among the subsystems.

In some embodiments, electronic device 900 includes a display subsystem 926 for displaying information on a display, which may include a display driver and the display, such as: a liquid-crystal display, a multi-touch touchscreen or a touch-sensitive display, an optical projector, a laser projector, a holographic display, or any other suitable display for displaying 2-dimensional or 3-dimensional images.

Moreover, electronic device 900 may include a security subsystem 932, which may include one or more biometric sensor(s) and/or may implement password authorization. For example, the one or more biometric sensors may include: a fingerprint scanner, a retina scanner, and/or another biometric sensor that can capture biometric information that is used for authentication and/or authorization.

Electronic device 900 can be (or can be included in) any electronic device with at least one network interface. For example, electronic device 900 can be (or can be included in): a desktop computer, a laptop computer, a subnotebook/netbook, a server, a workstation, a tablet computer, a smartphone, a cellular telephone, a smart watch, a consumer-electronic device, a portable computing device, an access point, a router, a switch, communication equipment, test equipment, a wearable appliance, and/or another electronic device.

Although specific components are used to describe electronic device 900, in alternative embodiments, different components and/or subsystems may be present in electronic device 900. For example, electronic device 900 may include one or more additional processing subsystems, memory subsystems, networking subsystems, display subsystems and/or audio subsystems. Additionally, one or more of the subsystems may not be present in electronic device 900. Moreover, in some embodiments, electronic device 900 may include one or more additional subsystems that are not shown in FIG. 9. Also, although separate subsystems are shown in FIG. 9, in some embodiments, some or all of a given subsystem or component can be integrated into one or more of the other subsystems or component(s) in electronic device 900. For example, in some embodiments program instructions 922 is included in operating system 924.

Moreover, the circuits and components in electronic device 900 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 914, such as a radio. Moreover, the integrated circuit may include hardware and/or software mechanisms that are used for transmitting wireless signals from electronic device 900 and receiving signals at electronic device 900 from other electronic devices. Aside from the mechanisms herein described, radios are generally known in the art and hence are not described in detail. In general, networking subsystem 914 and/or the integrated circuit can include any number of radios. Note that the radios in multiple-radio embodiments function in a similar way to the described single-radio embodiments.

In some embodiments, networking subsystem 914 and/or the integrated circuit include a configuration mechanism (such as one or more hardware and/or software mechanisms) that configures the radio(s) to transmit and/or receive on a given communication channel (e.g., a given carrier frequency). For example, in some embodiments, the configuration mechanism can be used to switch the radio from monitoring and/or transmitting on a given communication channel to monitoring and/or transmitting on a different communication channel. (Note that 'monitoring' as used herein comprises receiving signals from other electronic devices and possibly performing one or more processing operations on the received signals, e.g., determining if the received signal comprises an advertising frame, receiving the input data, etc.)

While communication protocols compatible with Ethernet and Wi-Fi or a cellular-telephone communication protocol were used as illustrative examples, the described embodiments of the testing technique may be used in a variety of network interfaces. Furthermore, while some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both. For example, at least some of the operations in the testing technique may be implemented using program instructions 922, operating system 924 (such as a driver for interface circuit 918) and/or in firmware in interface circuit 918. Alternatively or additionally, at least some of the operations in the testing technique may be implemented in a physical layer, such as hardware in interface circuit 918.

While program instructions 922 is illustrated as being resident on and executed by electronic device 900, in some embodiments a user of electronic device 900 may interact with a web page that is provided by another electronic device, and which is rendered by a web browser on electronic device 900. In some embodiments, at least a portion of program instructions 922 (such as software or an application) executing on electronic device 900 may be an application tool that is embedded in the web page, and that executes in a virtual environment of the web browser. Thus, the application tool may be provided to the user via a client-server architecture. Note that program instructions 922 executed by electronic device 900 may be a standalone application or a portion of another application that is resident on and that executes on electronic device 900.

In the preceding description, we refer to 'some embodiments.' Note that 'some embodiments' describes a subset of all of the possible embodiments, but does not always specify the same subset of embodiments. Moreover, note that the numerical values provided are intended as illustrations of the communication technique. In other embodiments, the numerical values can be modified or changed.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A method for performing a medical test by an electronic device, comprising:
    storing a biological sample associated with a biological life form, wherein the biological sample comprises a portion of the biological life form;
    performing one or more magnetic resonance (MR) measurements on at least a second portion of the biological life form using an MR measurement device;
    quantitatively simulating an MR response of at least the second portion of the biological life form;
    calculating a first test result by comparing the one or more MR measurements and the quantitative simulation, wherein the first test result is calculated using a forward model comprising multiple voxels representing at least the second portion of the biological life form, wherein the multiple voxels comprise at least $512^2$ voxels, wherein the forward model simulates magnetic-resonance response physics occurring within at least the second portion of the biological life form, wherein the calculating is based at least in part on: an external magnetic field, a radio-frequency pulse sequence, the model parameters of the multiple voxels, and one of: Bloch equations, or Liouvillian computations, wherein the model parameters comprise a density of a type of nuclei, a longitudinal relaxation time along a direction parallel to the external magnetic field and a transverse relaxation time along a direction perpendicular to the external magnetic field, and wherein the first test result comprises a diagnosis of a medical condition or is associated with a treatment for the medical condition;

determining one or more additional medical tests to perform that are predicted to improve an accuracy of the first test result, wherein the determining of the one or more additional medical tests is based at least in part on: additional medical knowledge since the biological sample was stored and the medical condition;

deciding to use a limited resource comprising the stored biological sample based at least in part on the predicted improved accuracy of the one or more medical tests;

obtaining at least a third portion of the biological sample by accessing the biological sample;

obtaining one or more additional test results by automatically performing the one or more additional medical tests on at least the third portion of the biological sample; and computing a second test result based at least in part on the first test result and the one or more additional test results, wherein the computing of the second test result comprises: computing an accuracy of the second test result, and computing that the second test result has an improved accuracy relative to the first test result.

2. The method of claim 1, wherein the biological sample is stored in a cryogenic repository; and wherein the storing comprises dividing and separately storing two or more portions of the biological sample.

3. The method of claim 1, wherein storing the biological sample comprises storing a longitudinal sequence of biological samples associated with the biological life form over a time interval.

4. The method of claim 1, wherein the determining comprises assessing benefits of a set of additional medical tests relative to costs of the set of additional medical tests and selecting the one or more additional medical tests.

5. The method of claim 1, wherein the one or more additional medical tests are performed automatically.

6. The method of claim 1, wherein the one or more additional medical tests comprise at least one of: a genetic test, a metabolic test, a biochemical test, a molecular test or cellular analysis.

7. The method of claim 1, wherein the calculation is based at least in part on an invariant MR signature of at least the second portion of the biological life form, the radio-frequency pulse sequence, a magnetic-field strength of the external magnetic field, a magnetic-field gradient of the external magnetic field, magnetic-field inhomogeneities of the MR measurement device, and a noise characteristic of the MR measurement device; and wherein the invariant MR signature characterizes an MR response of at least the second portion of the biological life form to MR measurement conditions that comprise the radio-frequency pulse sequence, the magnetic-field strength and the magnetic-field gradient selected from a range of pulse sequences, a range of magnetic-field strengths and a range of magnetic-field gradients.

8. The method of claim 7, wherein the invariant MR signature is determined using an inverse calculation based at least in part on additional MR measurements on at least the second portion of the biological life form or a different portion of the biological life form and the MR measurement conditions.

9. The method of claim 1, wherein the method comprises selectively providing a recommendation based at least in part on the second test result, the improved accuracy and a threshold value.

10. The method of claim 1, wherein the accessing comprises accessing one of a set of portions of the biological sample having a predefined aliquoted amount needed for the one or more additional medical tests.

11. A non-transitory computer-readable storage medium for use with an electronic device, the computer-readable storage medium storing program instructions, wherein, when executed by the electronic device, the program instructions cause the electronic device to perform one or more operations comprising:

storing a biological sample associated with a biological life form, wherein the biological sample comprises a portion of the biological life form;

performing one or more magnetic resonance (MR) measurements on at least a second portion of the biological life form using an MR measurement device;

quantitatively simulating an MR response of at least the second portion of the biological life form;

calculating a first test result by comparing the one or more MR measurements and the quantitative simulation, wherein the first test result is calculated using a forward model comprising multiple voxels representing at least the second portion of the biological life form, wherein the multiple voxels comprise at least $512^2$ voxels, wherein the forward model simulates magnetic-resonance response physics occurring within at least the second portion of the biological life form, wherein the calculating is based at least in part on: an external magnetic field, a radio-frequency pulse sequence, the model parameters of the multiple voxels, and one of: Bloch equations, or Liouvillian computations, wherein the model parameters comprise a density of a type of nuclei, a longitudinal relaxation time along a direction parallel to the external magnetic field and a transverse relaxation time along a direction perpendicular to the external magnetic field, and wherein the first test result comprises a diagnosis of a medical condition or is associated with a treatment for the medical condition;

determining one or more additional medical tests to perform that that are predicted to improve an accuracy of the first test result, wherein the determining of the one or more additional medical tests is based at least in part on: additional medical knowledge since the biological sample was stored and the medical condition;

deciding to use a limited resource comprising the stored biological sample based at least in part on the predicted improved accuracy of the one or more medical tests;

obtaining at least a third portion of the biological sample by accessing the biological sample;

obtaining one or more additional test results by automatically performing the one or more additional medical tests on at least the third portion of the biological sample; and computing a second test result based at least in part on the first test result and the one or more additional test results, wherein the computing of the second test result comprises: computing an accuracy of the second test result, and computing that the second test result has an improved accuracy relative to the first test result.

12. The non-transitory computer-readable storage medium of claim 11, wherein the biological sample is stored in a cryogenic repository; and
wherein the storing comprises dividing and separately storing two or more portions of the biological sample.

13. The non-transitory computer-readable storage medium of claim 11, wherein storing the biological sample comprises storing a longitudinal sequence of biological samples associated with the biological life form over a time interval.

14. The non-transitory computer-readable storage medium of claim 11, wherein the one or more additional medical tests are performed automatically.

15. The non-transitory computer-readable storage medium of claim 11, wherein the calculation is based at least in part on an invariant MR signature of at least the second portion of the biological life form, the radio-frequency pulse sequence, a magnetic-field strength of the external magnetic field, a magnetic-field gradient of the external magnetic field, magnetic-field inhomogeneities of the MR measurement device, and a noise characteristic of the MR measurement device; and
wherein the invariant MR signature characterizes an MR response of at least the second portion of the biological life form to MR measurement conditions that comprise the radio-frequency pulse sequence, the magnetic-field strength and the magnetic-field gradient selected from a range of pulse sequences, a range of magnetic-field strengths and a range of magnetic-field gradients.

16. The non-transitory computer-readable storage medium of claim 15, wherein the invariant MR signature is determined using an inverse calculation based at least in part on additional MR measurements on at least the second portion of the biological life form or a different portion of the biological life form and the MR measurement conditions.

17. An electronic device, comprising:
an interface circuit configured to communicate with at least another electronic device;
a processor coupled to the interface circuit; and
memory, coupled to the processor, which stores program instructions, wherein, when executed by the processor, the program instructions cause the system to perform one or more operations comprising:
storing a biological sample associated with a biological life form, wherein the biological sample comprises a portion of the biological life form;
performing one or more magnetic resonance (MR) measurements on at least a second portion of the biological life form using an MR measurement device;
quantitatively simulating an MR response of at least the second portion of the biological life form;
calculating a first test result by comparing the one or more MR measurements and the quantitative simulation, wherein the first test result is calculated using a forward model comprising multiple voxels representing at least the second portion of the biological life form, wherein the multiple voxels comprise at least $512^2$ voxels, wherein the forward model simulates magnetic-resonance response physics occurring within at least the second portion of the biological life form, wherein the calculating is based at least in part on: an external magnetic field, a radio-frequency pulse sequence, the model parameters of the multiple voxels, and one of: Bloch equations, or Liouvillian computations, wherein the model parameters comprise a density of a type of nuclei, a longitudinal relaxation time along a direction parallel to the external magnetic field and a transverse relaxation time along a direction perpendicular to the external magnetic field, and wherein the first test result comprises a diagnosis of a medical condition or is associated with a treatment for the medical condition;
determining one or more additional medical tests to perform that that are predicted to improve an accuracy of the first test result, wherein the determining of the one or more additional medical tests is based at least in part on: additional medical knowledge since the biological sample was stored and the medical condition;
deciding to use a limited resource comprising the stored biological sample based at least in part on the predicted improved accuracy of the one or more medical tests;
obtaining at least a third portion of the biological sample by accessing the biological sample;
obtaining one or more additional test results by automatically performing the one or more additional medical tests on at least the third portion of the biological sample; and
computing a second test result based at least in part on the first test result and the one or more additional test results, wherein the computing of the second test result comprises:
computing an accuracy of the second test result, and computing that the second test result has an improved accuracy relative to the first test result.

18. The system of claim 17, wherein storing the biological sample comprises storing a longitudinal sequence of biological samples associated with the biological life form over a time interval.

19. The system of claim 17, wherein the calculation is based at least in part on an invariant MR signature of at least the second portion of the biological life form, the radio-frequency pulse sequence, a magnetic-field strength of the external magnetic field, a magnetic-field gradient of the external magnetic field, magnetic-field inhomogeneities of the MR measurement device, and a noise characteristic of the MR measurement device; and
wherein the invariant MR signature characterizes an MR response of at least the second portion of the biological life form to MR measurement conditions that comprise the radio-frequency pulse sequence, the magnetic-field strength and the magnetic-field gradient selected from a range of pulse sequences, a range of magnetic-field strengths and a range of magnetic-field gradients.

20. The system of claim 19, wherein the invariant MR signature is determined using an inverse calculation based at least in part on additional MR measurements on at least the second portion of the biological life form or a different portion of the biological life form and the MR measurement conditions.

* * * * *